United States Patent [19]
Walker et al.

[11] Patent Number: 5,646,178
[45] Date of Patent: Jul. 8, 1997

[54] CRANBERRY EXTRACT AND BIOLOGICALLY ACTIVE COMPOUNDS DERIVED THEREFROM

[75] Inventors: Edward B. Walker; Richard A. Mickelsen, Jr.; Jennifer N. Mickelsen, all of Ogden, Utah

[73] Assignee: JLB, Inc., Ogden, Utah

[21] Appl. No.: 473,864

[22] Filed: Jun. 7, 1995

Related U.S. Application Data

[63] Continuation-in-part of Ser. No. 409,703, Mar. 24, 1995, and Ser. No. 189,889, Feb. 1, 1994, Pat. No. 5,525,341, which is a continuation-in-part of Ser. No. 959,222, Oct. 9, 1992, abandoned.

[51] Int. Cl.$^6$ ............... A61K 31/16; A61K 31/045; A61K 31/725; A61K 35/78
[52] U.S. Cl. ............ 514/456; 514/724; 514/56; 424/195.1
[58] Field of Search ................ 514/456, 724, 514/54; 424/195.1

[56] References Cited

U.S. PATENT DOCUMENTS

| | | | |
|---|---|---|---|
| 3,963,700 | 6/1976 | Philip | 536/4.1 |
| 4,083,779 | 4/1978 | Combe et al. | 410/23 H |
| 4,309,207 | 1/1982 | Devlin | 71/79 |
| 4,652,448 | 3/1987 | Sadowski | 424/87 |
| 4,775,477 | 10/1988 | Stahl et al. | 210/641 |
| 4,857,327 | 8/1989 | Virdalm | 424/195.1 |
| 5,128,100 | 7/1992 | Hollis et al. | 422/14 |
| 5,200,186 | 4/1993 | Gabetta et al. | 424/195.1 |

FOREIGN PATENT DOCUMENTS

| | | | |
|---|---|---|---|
| 1054899 | 10/1991 | China . | |
| 3027933 | 2/1981 | Germany . | |
| 3427014 | 1/1986 | Germany . | |
| 9013304 | 11/1990 | WIPO | A61K 35/78 |
| 9206695 | 4/1992 | WIPO | A61K 35/78 |

OTHER PUBLICATIONS

CRC Handbook of Fruit Set and Development; pp. 114, 115 and 117.
Marwan et al.; "Microbial Inhibitors of Cranberries"; Journal Food Science; vol. 51, No. 4; 1986; pp. 1009–1013.
Sobota; "Inhibition of Bacterial Adherence by Cranberry Juice: Potential Use for the Treatment of Urinary Tract Infections"; The Journal of Urology; vol. 131; 1984; pp. 1013–1016.
Fuleki et al.; "Quantitative Methods for Anthocyanins. 1. Extraction and Determination of Total Anthocyanin in Cranberries"; Journal of Food Science; vol. 33; 1968; pp. 72–77.
Fuleki et al.; "Quantitative Methods for Anthocyanins. 3. Purification of Cranberry Anthocyanins"; Journal of Food Science; vol. 33; 1968; pp. 266–274.
Ofek et al.; "Anti–*Escherichia coli* Adhesion Activity of Cranberry and Blueberry Juices"; vol. 324, No. 22; p. 1599.
Zafriri et al.; "Inhibitory Activity of Cranberry Juice on Adherence on Type 1 and Type P Fimbriated *Escherichia coli* to Euracroytic Cells"; Antimicrobial Agents & Chemotherapy; vol. 33, No. 1; 1989; pp. 92–98.
Official Methods of Analysis of the Association of Official Analytical Chemists; 1984; pp. 424–425.
Puski et al.; "Flavonol Glycosides in Cranberries"; Journal of Food Science; vol. 32; 1967; pp. 527–530.
The Merck Index, An Encyclopedia of Chemicals, Drugs, and Biologicals; 1989; pp. 291, 452, 453, 650, 857, 941, 999.
Sephadex LH–60 Chromatography in Organic Solvents, Pharmacia Fine Chemicals.
Sunset Western Garden Book; 1988; pp. 207, 208, 435 and 436.
Wang et al.; "Isolation and Characterization of Polyphenolic Compounds in Cranberries"; Journal of Food Science; vol. 43, No. 5; 1978; pp. 1402–1404.
Welsh et al.; "Great Basin Naturalist Memoirs A Utah Flora"; Brigham Young University, Provo, Utah; No. 9; 1987; pp. 605.
Payless Drug Stores Coupon, "Cranberry Extract" advertisement.

*Primary Examiner*—John W. Rollins
*Attorney, Agent, or Firm*—Trask, Britt & Rossa

[57] ABSTRACT

Compounds isolated from plant materials of the genus Vaccinium, which have biological activity measurable as inhibition with adhesion of bacterial cells to surfaces, are described. The specific compounds include procyanidins, leucocyanin and leucodelphinin, and flavonol glucosides including myricetin-3-pyranoside. An exemplary procyanidin compound is a substituted epicatechin-catechin dimer or other polymer. Also described is an extract prepared from plants of the genus Vaccinium, especially cranberries, which is enriched for anti-adhesion activity. The extract is enriched for polyphenol and flavonoid compounds, lacks detectable amounts of simple sugars, has a very low content of benzoic acid relative to raw cranberries, and lacks significant amounts of anthocyanins. Methods for preparing and for using the extract are disclosed.

33 Claims, 23 Drawing Sheets

CRANBERRY EXTRACT AND BIOLOGICALLY ACTIVE COMPOUNDS DERIVED THEREFROM

RELATED APPLICATION

This application is a continuation-in-part of application U.S. Ser. No. 08/189,889 filed on Feb. 1, 1994, now U.S. Pat. No. 5,525,341, which is a continuation-in part of U.S. Ser. No. 07/959,222, filed Oct. 9, 1992, now abandoned. This application is also a continuation-in-part of co-pending application U.S. Ser. No. 08/409,703 filed on Mar. 24, 1995. The contents of all these related applications are incorporated by this reference.

TECHNICAL FIELD

THE invention relates to plant extracts having therapeutic and other uses, and more particularly to an extract of Vaccinium species.

BACKGROUND

May persons consider cranberry juice and derivatives to be beneficial to health, and products including powders made from cranberries or cranberry juices are commercially available. Doctors often recommend cranberry products to patients suffering from urinary tract infections. However, most available preparations, as well as raw cranberries and typical cranberry juice products, have a relatively high acidity. This acidity can cause stomach upset and produce a sour taste, which is unappealing to many people. Consequently, a need exists for a cranberry extract that includes the active fraction of cranberries responsible for its perceived beneficial actions.

DISCLOSURE OF THE INVENTION

The invention includes methods of utilizing extracts of Vaccinium, and compounds derived therefrom, to interfere with microbial adhesion to a surface such as body tissue. Such body tissues include tissues associated with the mouth, such as the gums, teeth and oral cavity mucosal tissues, throat tissues, genital tissues, and cervical surface tissues. The invention thus includes the use of the Vaccinium extracts and derived compounds to treat various maladies such as urinary tract infections.

The invention also includes various extracts of Vaccinium and processes for obtaining these extracts.

The invention includes the use of compounds isolated from plant materials of the genus Vaccinium, which components have biological activity measurable as inhibition with adhesion of bacterial cells to surfaces, and an extract of such plant materials which is significantly enriched for this anti-adhesion activity. The specific compounds used include procyanidins, leucocyanin and leucodelphinin, and flavonol glucosides including myricetin-3-pyranoside. An exemplary, preferred procyanidin compound is a substituted epicatechin-catechin dimer.

These components have a structure selected from I, II, and III, and their esters, or ethers or the corresponding oxonium salts thereof,

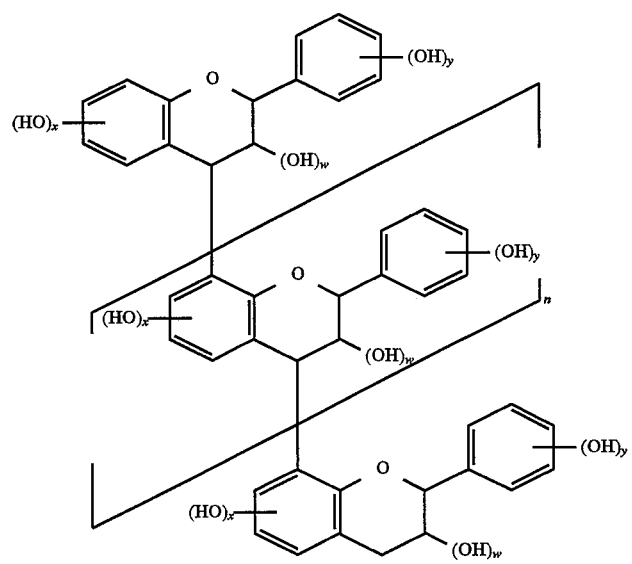

I

-continued

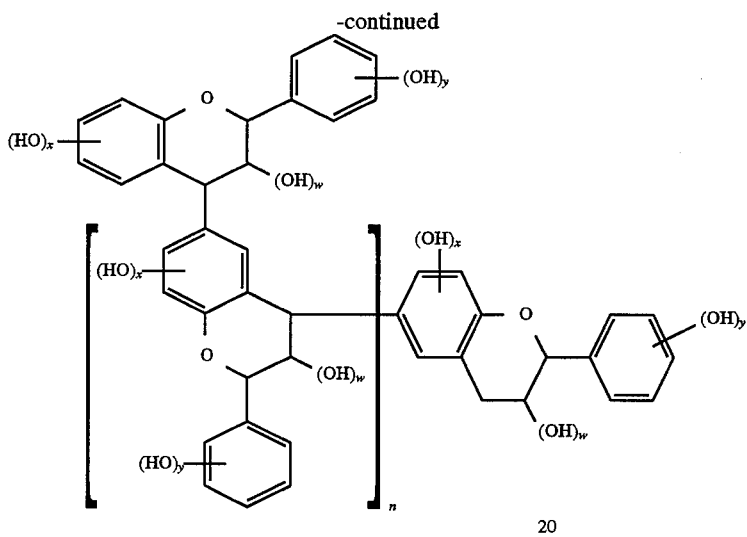

II

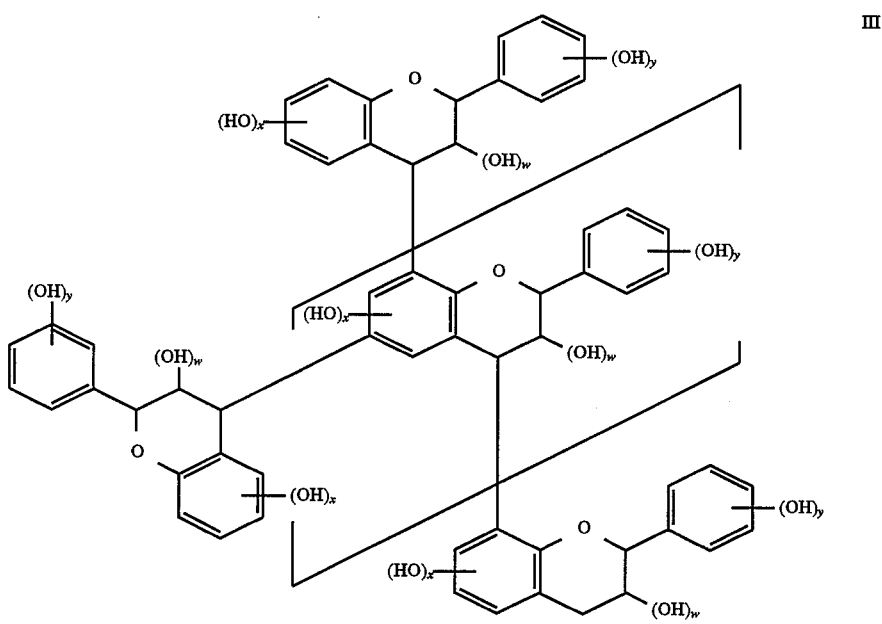

III wherein x=1 to 3, y=1 to 3, w=0 or 1, n=0 to 18, preferably 0 to 15, more preferably 0 to 11, wherein x=1 to 3, y=1 to 3, z=1 or 2.

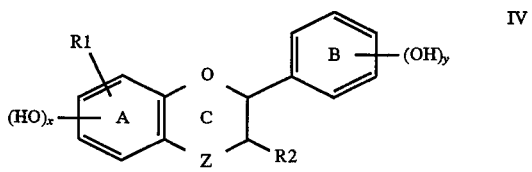

IV

The proanthocyanidin polymer useful for treating non-viral microbial infection can comprise 2 to 18 monomeric flavanoid units having structure IV, or esters, ethers or corresponding oxonium salts thereof. In (IV), x is 0 to 3; y is 0 to 3; is $CH_2$, CHOH, C=O, $CHSO_3H$, galloyl, catechin, or epicatechin; R1 is H, pyranoside, galloyl, catechin, or epicatechin; and R2 is H, OH, pyranoside, or galloyl.

Prodrug Concept:

Another aspect of the invention includes the metabolically-altered or activated polyphenolic substances described. According to the literature (Hackett, et al., (1983) Xenobiotica 13(5), 279–86 and ibid., 12(7), 405–16) 90% of the disclosed polyphenolic substances are metabolized into and excreted as catechin glucuronide and/or 3'-o-methyl-(+)-catechin glucuronide and/or 3'-o-methyl-(+)-catechin sulfate [82249-08-9], preserving the intact flavanol ring system. These metabolically activated substances include compounds and other chemically-activated glucuronides and/or sulfates of phenolic substances such as epicatechin, catechin, myrecitin, quercitin, quercitin, rutin, and the like.

| Example; catechin: | x = 2, y = 2 |
|---|---|
| activated by metabolism or other chemical means. | R1 = —H or —$SO_3H$<br>R2 = —H or —$SO_3H$ or —$CH_3$ |

Another aspect of the invention relates to a method of treating non-viral infections comprising administering, to a warm-blooded animal, a therapeutically effective amount of anti-adherence agent comprising a proanthocyanidin monomer or polymer containing 2 to 28 flavonoid units, preferably 2 to 15 flavonoid units and more preferably 2 to 11 flavonoid units. The flavonoid units include but are not limited to catechins, epicatechins, gallocatechins, galloepicatechins, flavanols, flavonols, flavandiols, leucocyanidins, leucodelphinidin anthocyanidins, or combinations thereof. The flavonoid units can be singly or double linked to each other. The proanthocyanidin polymer can be administered intravenously, intraperitoneally, subcutaneously, intramuscularly, orally, topically, or by inhalation.

The present invention also relates to proanthocyanidins useful for treating non-viral infections in general having a structure selected from I, II, and III, above, and esters, ethers and corresponding oxonium salts thereof, where n=0 to 28, preferably 0 to 13, most preferably 0 to 9.

When the extract is analyzed by reverse-phase HPLC on a C18 lipophilic column, characteristic sets of elution peaks of compounds absorbing at 230 nanometers ("nm"), 280 nm and 360 nm are observed. When subjected to further purification, one of the 280 nm-absorbing peaks is found to contain the exemplary procyanidin. The flavonol glucosides are purified from 360 nm-absorbing elution peaks. The pyranoside moiety in these compounds may be glucose, mannose, or a like sugar.

In one embodiment of the invention, the extract is enriched by at least about 500- to 1500-fold for the bacterial anti-adhesion activity, as compared with juices which are 100% derived from the plant material. The extract is enriched to a similar degree in the concentration of flavonoid and other polyphenol compounds detected by spectroscopic methods.

In one aspect, the extract may be very low in acid and in simple sugars, with a benzoic acid content typically less than about 0.01 milligrams per gram dry powder, and essentially undetectable amounts of free monomer or dimer sugars. The extract is prepared from cranberries (*V. macrocarpon* and variants), *V. myrtilis* (bilberry), *V. oxycoccus* (European cranberry), or *V. corymbosum* (blueberries).

The extract has a greatly-reduced content of both acids and sugar, and is a food supplement to replace cranberries and cranberry juice. The low sugar and acid content make the extract highly suitable for oral hygiene products, and more useful to those who seek the health benefits of a cranberry extract product.

The invention also includes a method of making an extract having the aforementioned properties and a method of inhibiting the adhesion of bacteria to surfaces using the extract.

A method of making the extract includes preparing a starting extract from plants or plant parts of species selected from the genus Vaccinium, this starting extract including charged and polar compounds and the active fraction; concentrating the extract to a smaller volume; and enriching the extract for the active fraction and for polyphenol and flavonoid compounds generally. The method may also include removing most of the free monomer and dimer sugars from the extract; removing most of the benzoic acid from the extract; and removing monomeric anthocyanins. Techniques are described for accomplishing each of the indicated steps by chromatography or by precipitation and phase extraction steps. Additionally, in one embodiment the method includes a step of mannose affinity chromatography, which selects for compounds that can compete for binding to a mannose-affinic substrate.

The invention embraces compositions produced by first extracting active compounds from plant materials with water or solvents such as, but not limited to, alcohols, acetone, acetonitrile, or ethyl acetate, or miscible mixtures of these solvents, water or MeOH/water or acetone/water mixtures preferred, leaving a pulp or residue significantly depleted for the anti-adhesion fraction. Alternatively, the plant materials may be extracted with relatively non-polar organic solvents such as but not limited to hexane, heptane, cyclohexane, methylene chloride, chloroform, or large molecular weight alcohols that contain more than 8 carbon atoms, and the like. Such treatment extracts non-active materials, leaving a pulp or residue with increased concentrations of active substances. This pulp or residue may be further processed by extraction with more polar solvents such as, but not limited to water, alcohols with fewer than 8 carbon atoms, acetone, acetonitrile, ethylacetate, or miscible mixtures of these solvents to further enrich the active fraction.

The anti-adhesion property of the extract is useful in a number of areas. For example, the cleaning of industrial fermentation equipment, medical and dental instruments, laboratory culture jars, and the like may be accomplished with the extract. The extract may further be useful in inhibiting the adhesion of bacteria to surgical implants, tooth surfaces, and oral cell types found in the mouth, and to cells in the urinary tract of humans and/or animals.

A method of inhibiting the adhesion of bacteria includes the steps of providing an extract as described and applying the extract in a suitable medium to a surface believed to have bacteria such as *E. coli* adhered thereto to disengage the bacteria from the surface(s). The method is useful to inhibit the adhesion of bacteria to such surfaces as teeth, other bacteria adhered to teeth, human oral epithelial cells, and human epithelial urinary tract cells; and to clean dental implants, bacterial fermentation vats, and the like.

BEST MODE OF THE INVENTION

An extract of species of the genus Vaccinium, which is highly enriched for an active fraction having activity to inhibit the adherence of certain bacterial species to various substrates, is also highly enriched in the content of flavonoids and polyphenols. The extract may be in powdered form or dissolved in a suitable solvent. The powdered form described herein is a reddish-brown powder having a density of about 0.43±0.03 g/cc and other properties as described herein. For convenience and clarity, the extract will be referred to hereinafter as the "enriched extract," and, when reference is made to an extract made from a particular species such as cranberries, as the "cranberry extract."

Figure 1:
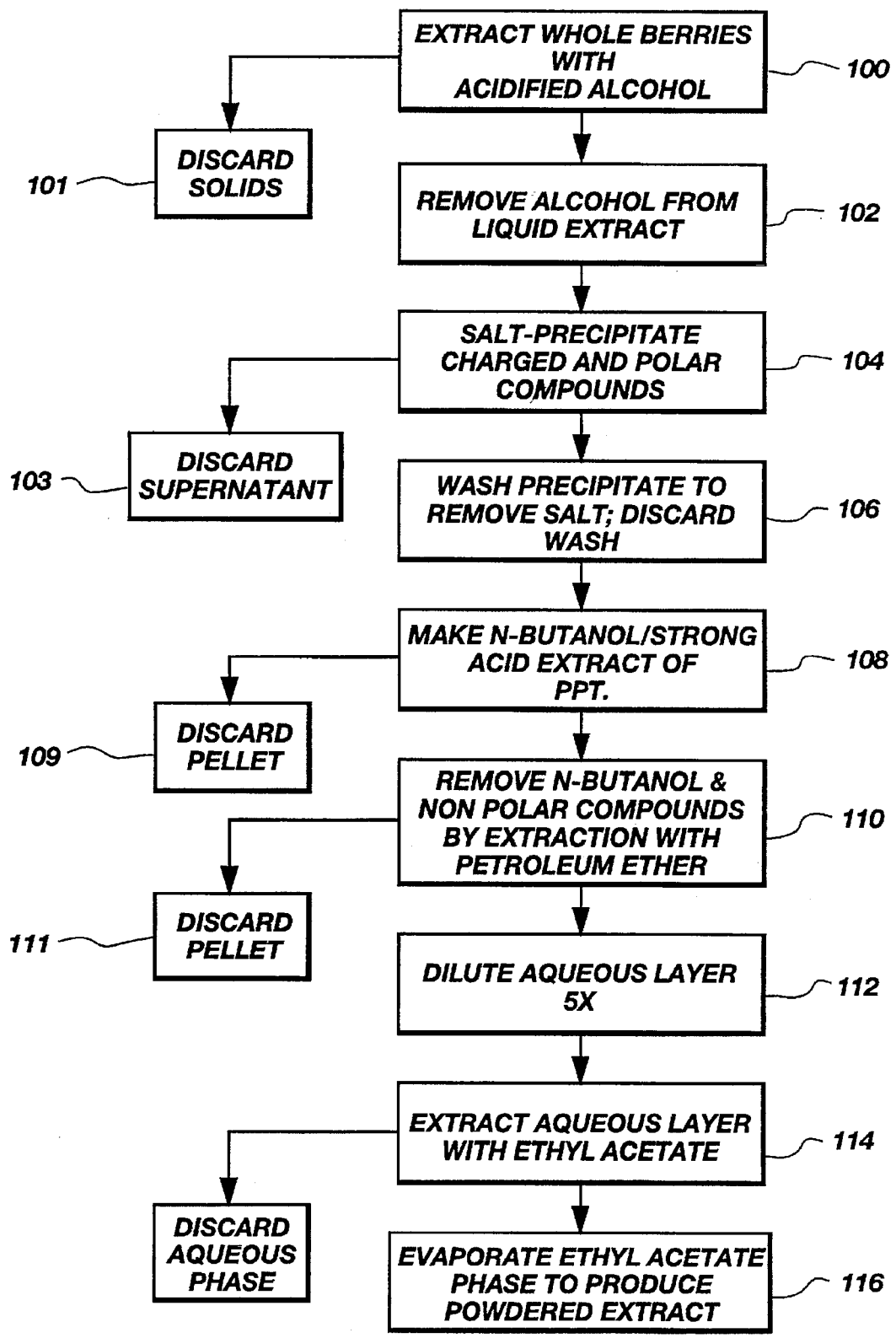
FIG. 1 is a flow chart for preparing an extract according to the invention.

A. Processes:

An extract having the characteristics of the enriched extract described herein may be prepared by the steps illustrated in FIG. 1. Except for the final non-polar solvent extraction, which selectively removes anthocyanins, this method is similar to a standard method used to extract anthocyanins from plant materials (see, e.g., *Official Methods of Analysis of the Association of Official Analytical Chemists*, §§22.092 through 22.095 et seq., pp. 424–425 (1984); also Fuleki and Francis, "Purification of Cranberry Anthocyanins," *J. Food Science* 33:266–274 (1966)). Anthocyanins are flavonoid compounds closely related to, and often co-isolated with, polyphenols. However, cranberry-derived anthocyanins isolated by the previously-described methods did not significantly inhibit bacterial adhesion to surfaces. Moreover, cranberry extract, which is about 1000-fold enriched for the adhesion-inhibiting activity, has low or no levels of anthocyanins. Anthocyanins characteristically exhibit strong absorption of 512 nm light. From the chromatograms of FIGS. 5A and 5B, it is apparent that the levels of anthocyanins in the extract were much lower than the levels of polyphenol components absorbing at about 360 nm.

The method depicted in FIG. 1 also removes substantially all free simple sugars and most of the benzoic acid from the enriched extract. However, other methods are known for concentrating and purifying polyphenols and related compounds such as flavonoids, anthocyanins and catechols from cranberries and other plant materials (see, e.g., Puski and Francis, "Flavonol Glycosides in Cranberries," *J. Food Science* 32:527–530 (1967); Fuleki and Francis, "Quantitative Methods for Anthocyanins: Purification of Cranberry Anthocyanins," *J. Food Science* 33:266–274 (1968); P. L. Wang et al., "Isolation and Characterization of Polyphenolic Compounds in Cranberries," *J. Food Science* 43:1402–1404 (1978)). These other methods may also produce an extract enriched for anti-adhesion activity, but having greater or lesser amounts of peripheral substances such as the previously-mentioned sugars, benzoic acid, and anthocyanins.

A method for preparing an enriched extract is as follows. First, polar and charged compounds including anthocyanins and other flavonoid and polyphenol compounds are extracted from selected plant material of plants of the genus Vaccinium (step 100). Preferably, the selected plant material is berries or fruits (e.g., cranberries).

Also, it has been found that in lieu of fresh or frozen berries, another useful starting material is an aqueous solution of a powdered cranberry product (commercially available as OCEAN SPRAY™ brand). This solution may be used in place of the acidified alcohol-water extract of whole berries (steps 100–102 of FIG. 1). The cranberry powder is believed to be obtained by spray-drying an aqueous extract of the raw cranberry material. A solution of 10 to 20% by weight of powdered cranberry is a starting material that has yielded good results. Higher concentrations of this powder are less desirable. In a procedure starting with such a cranberry solution, steps 100 and 102 of the extraction of FIG. 1 are eliminated.

Step 100 involves crushing the plant material, mixing the material with a large volume of acidified alcohol, and thoroughly agitating the mixture. The acidified alcohol preferably comprises a fairly polar alcohol and water in about equal proportions, with a suitable acid in an amount of about 1 to about 10% by volume. In a preferred embodiment, the proportions are 10:1:10 ethanol:acetic acid:water. Suitable alcohols also include methanol ("MeOH"), ethanol ("EtOH"), and propanol, and suitable acids include acetic acid ("HOAc"), hydrochloric acid ("HCl"), and phosphoric acid ("$H_3PO_4$"). The solid residue is separated from the liquid portion and the residue is disposed of.

Step 100 thus produces a liquid extract containing mainly polar and/or charged compounds including the active fraction, with a solid residue of plant material debris containing largely nonpolar compounds.

The liquid extract is then concentrated to about 4–6% of the original volume of extract (step 102) by removing a substantial part of the alcohol. Preferably, the extract is evaporated to perhaps about 1–5% of the original volume of liquid extract, and then water is added to bring it up to 4–6% of the original volume. A concentrated liquid extract results.

In step 104, monomer and dimer sugars are substantially removed from the concentrated extract. For example, a metal acetate or sulfate is added to the concentrated liquid extract, which precipitates a solid, leaving the simple sugars in solution. The precipitate includes complexes of the active fraction with the metal. Step 104 may be carried out by adding sufficient metal compound to the extract (a concentration of about 1 to 1.1 molar), followed by the addition of about 0.4 volumes of a volatile inorganic base to the concentrated extract, with thorough mixing. The inorganic base is preferably rather strong (e.g. $NH_4OH$). The solid precipitate forms rather quickly after addition of the base.

When use of a lead compound (e.g., lead acetate) as the metal salt of step 104 is undesirable, other metal salts may be used, for example, acetates of zinc, magnesium, nickel, barium and calcium, cobalt or sodium, or zinc sulfate. Zinc acetate, magnesium acetate, and zinc sulfate are preferred. Nickel, barium and calcium acetates produced an enrichment of 60–80% relative to that achieved with zinc acetate (taken as 100%), while sodium acetate and cobalt acetate gave relative yields of only 20–40%.

The precipitated solids may be washed with a large amount of a polar alcohol, such as 80% EtOH in water, to remove excess salt and traces of monomer and dimer sugars (step 106). MeOH or propanol may be substituted for EtOH.

The solids are then mixed with n-butanol and concentrated HCl, in a proportion of about 6:1 (step 108). The acidic n-butanol removes the metal ion and solubilizes the active fraction, while the HCl is believed to alter the relative polarity of the active components to thereby render them soluble in n-butanol. Although n-butanol is presently preferred, other moderately polar solvents (e.g., i-butanol, t-butanol, pentanol or hexanol) may be used. An alcohol liquid phase and a pellet comprising mostly metal chloride results. The pellet is discarded (step 109).

The butanol is then removed from the liquid phase of step 108 by extraction with a nonpolar organic solvent such as petroleum ether (step 110). About three to ten volumes of the organic solvent are added to the alcohol liquid phase and vigorously mixed, then let stand to allow separation into a hydrophobic first organic phase comprising petroleum ether and butanol, and a first aqueous phase which contains the active fraction. The first aqueous phase, which is generally orange-red to red-brown in color (presumably due to the presence of anthocyanins), is separated from the organic layer and diluted with about 4 volumes of water (step 112).

The first organic phase may then be back-extracted with water (1/20 volume) until all of the red color has been removed from the first organic phase. The water layers from the back-extractions may then be combined with the aqueous phase of step 110, before the dilution step of 112.

After dilution, the first aqueous phase is then further extracted with a moderately polar organic such as ethyl acetate ("EtAc") (step 114) to produce a second organic phase containing the active fraction and a second aqueous phase in which a substantial proportion of the anthocyanins remains. Preferably, the first aqueous phase is extracted three times sequentially with about an equal volume of EtAc, and the three EtAc phases are pooled. Alternatively, the extraction step 114 may be performed as two sequential extractions, the first with an equal volume of diethyl ether ("Et$_2$O"), and the second with an equal volume of ethyl acetate.

In the process depicted in FIG. 1, it has been found that in the step of EtAc extraction (step 114), a significantly higher yield, both in terms of mass and in terms of activity level per unit mass, is obtained if the extraction is performed under acidic conditions (e.g., pH<about 2). Acidification may be accomplished by addition of HCl or other suitable acid.

In any case, following extraction step 114, the second organic phase is separated from the second aqueous phase and evaporated to leave a paste or powder (in one instance, a powder having a generally orange color and a density of about 0.43 g/cm$^3$ with a solubility in water of about 8.5 g/ml). This product will, for convenience, be termed a "flavonoid-enriched extract," which is consistent with the spectral data indicating enrichment for flavonoid-containing compounds. However, the term is not intended as limiting the active fraction of the extract to flavonoids or the like. The anthocyanins are substantially selectively retained in the second aqueous phase of extraction 114, although some may remain in the second organic phase. However, the second aqueous phase has considerably less anti-adhesion activity than does the second organic phase.

The extract prepared by this process is enriched about 1000-fold for an active fraction, which inhibits the adhesion of bacteria, including *E. coli* and *P. aeruginosa*, to mammalian cells and to certain surfaces. There is no detectible protein, and little or no free monomer and dimer sugars, in the enriched extract. The caloric value of the extract is generally less than about 4 calories per gram. Also, the acid content of the enriched extract, especially the benzoic acid content, is considerably lower than that of Vaccinium berries and of many other cranberry extract or powder products.

A variety of methods may be used to obtain an initial aqueous Vaccinium extract from which the anti-adhesion activity may be obtained. Table VIII includes a comparison of activity obtained using a variety of extraction methods.

Figure 10:
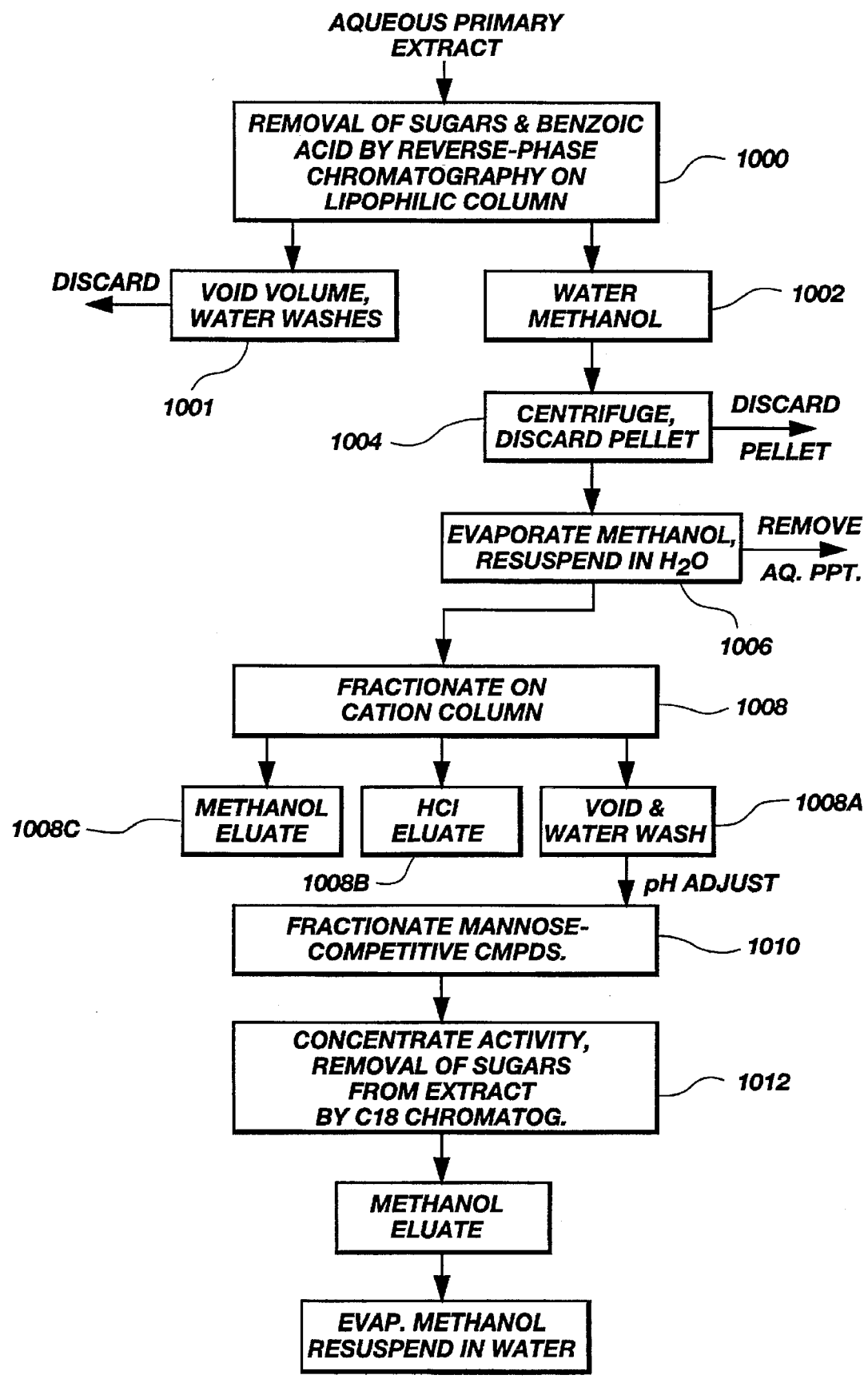
FIG. 10 is a flow chart depicting the steps of an alternate method for preparing an extract according to the invention.

Another method is depicted in FIG. 10. This method involves processing the initial aqueous extract largely by chromatographic separation steps instead of by precipitations, phase separations, etc. This embodiment is convenient and reduces the use of organic solvents. However, the chromatographic embodiment is still directed to the fundamental steps of enriching for charged and polar compounds, removing monomer and dimer sugars, removing benzoic acid and other organic acids, and removing anthocyanins, and these steps could be accomplished by substituting the appropriate steps previously described in reference to FIG. 1. That is, a "hybrid" embodiment combining certain steps from the embodiment of FIG. 1 and some from the embodiment of FIG. 10 may also produce the desired extract.

For example, in the embodiment of FIG. 10, the removal of simple sugars and benzoic acid from the extract (steps 1000, 1008, 1012 of FIG. 10) is accomplished by reverse-phase affinity chromatography on a lipophilic column, such as the C18 column, which is also used for HPLC analysis of the extract (step 1000).

The chromatographic embodiment may desirably include a further step of selectively separating compounds which compete with mannose for binding to a mannose-affinic substrate. This step is accomplished by subjecting the extract to affinity chromatography on a mannose-binding substrate bond to a support. In the present working examples, a concanavalin-A (abbreviated conA) column (Sigma Chemical Co. of St. Louis, Mo.) is used. ConA is known to bind mannose, and mannose binds to type 1 pill and interferes thereby with the pili-mediated adhesion of type 1 pili. In the conA affinity chromatographic step, the extract is passed over the column to cause selected components to bind to the conA and non-conA-binding compounds are washed from the column. A solution containing a sufficient excess of mannose or a mannose derivative is then used to elute the selected components from the column by competition.

Other mannose-binding agents could be similarly used for a mannose affinity chromatography separation. One alternate embodiment involves isolating the pili and/or the mannose binding region of the pili, and using this in place of conA for affinity chromatography. However, conA-conjugated supports are commercially available and thus convenient.

The mannose affinity chromatography may be performed after the extract has been partially purified by other steps. For example, the extract should already be free of simple sugars that could bind to conA and thus interfere with the binding of the desired polyphenol and flavonoid compounds.

The first step 1000 (FIG. 10) of the procedure is to remove the monomer and dimer sugars and benzoic acid from a primary aqueous Vaccinium extract by subjecting the primary extract to reverse-phase liquid chromatography on a lipophilic column. The primary extract can be obtained by making an aqueous solution of a powdered starting material as described above, by making an acidified alcohol extract as by steps 100–102 of the method of FIG. 1, or by equivalent other means.

In one embodiment, the reverse-phase chromatography of step 1000 is performed on a C18 cartridge column (Waters C18 "BondaPak", 10 μm beads, available from Millipore Corp. of Milford Mass, cat. #WAT038505). A 50-ml C18 cartridge column is prepared essentially according to the manufacturer's directions, by flushing first with 100 ml MeOH and then with 200 ml distilled water at a flow rate of 4–6 ml/min. From 350 ml to about 500 ml of the aqueous primary extract is then loaded onto the C18 column at a flow rate of 0.5 to about 2.0 ml/minute. If the fluid leaving the column during loading becomes pink or red in color, the column is being saturated. The column is then washed with an excess of water (800–1000 ml, or a sufficient amount until the eluant appears colorless or faint pink), at a flow rate of about 4–6 ml/min, to remove the sugars. Next, a sufficient volume of MeOH, typically about 150 to about 300 ml, is run through the column to elute the desired compounds. The MeOH eluate should be a deep red; when the eluate becomes pale pink, sufficient MeOH has passed through the column. The MeOH eluate usually contains precipitate, which is readily removed by centrifugation at 1500 to 5000 rpm with, for example, a tabletop or slightly larger centrifuge (step 1004). The precipitate is removed and the supernatant possesses the desired activity.

The MeOH of the MeOH supernatant of step 1002 is then evaporated under vacuum, and the residue is redissolved in about 25 ml warm water, preferably with sonication (step 1004). The sample may be centrifuged or filtered with a Whatman #1 filter to remove precipitate, which is discarded.

The aqueous sample is then subjected to chromatographic separation on a cation column (step 1008). A 4 to 8 ml cation column is prepared, as generally known, from a slurry of cation material in water. A presently-preferred cation material is the Waters Accell+CM Cation, which is a silica bead with a hydrophilic bonded layer having carboxymethyl as the available cation group (Millipore Corp. of Milford Mass). In a typical procedure, the aqueous sample, which has a volume of about 5 ml, is carefully loaded directly onto the cation column. At this point, a green color will be observed in the column and a very dark green material at the top of the column. The column is then washed with about 25 ml of distilled water (step 1008A). The dark green material at the very top washes out, only very slowly with plain water, and is desirably left behind.

The initial loading solution and the water wash (the void volume; step 1008A) of the cation column contain a substantial amount of the desired anti-adhesion activity. A substantial portion of anthocyanins are removed from the extract by the cation column, as revealed by analytic C18 chromatography of products of steps 1006 and 1008A (which may also be subjected to the optional CHCl$_3$/EtAc extraction). Desirably, the column is now washed with 1–2 column volumes of 1% HCl (aq) (step 1008B), which elutes essentially all of the green material. The HCl eluate has been found to consist mostly of anthocyanins. Following the HCl elution, a step of MeOH elution (step 1008C) is then performed. The MeOH eluate 1008C, upon evaporation and resuspension in water, surprisingly exhibits a substantial amount of anti-adhesion activity. The MeOH eluate compound(s) have significant HPLC elution peaks observable by absorbance at 230, 280 and 360 nm.

The void volume eluate 1008A is then concentrated (e.g., by evaporation) to a concentration of less than about 60 mg/ml, in preparation for affinity chromatography on a conA column. A 3 to 10 ml column of conA-bound column material (Sigma Chem. Co. of St. Louis Mo., cat. #C-9017) is prepared and flushed with 100 ml of phosphate buffer (0.05M sodium phosphate adjusted to pH 7 with H$_3$PO$_4$) at a flow rate of about 1 ml/min. Two ml of the aqueous eluate, containing no more than 60 mg/ml sample, is adjusted to the same concentration of conA phosphate buffer and applied to the column. After loading, the column is washed with about 50 ml of phosphate buffer or until the eluate is clear, again at about 1 ml/min. Finally, the column is eluted with at least 50–100 ml of phosphate buffer containing 10% α-methylmannopyranoside. The mannopyranoside compound is preferred over mannose for this purpose because it binds more tightly to the conA, and thus is expected to more effectively elute compounds bound to the mannose-affinic site on conA. A 10% concentration of α-methylmannopyranoside is found to be more efficient at eluting the active fraction than a lower concentration of 2%.

The resulting conA-eluate is then subjected to another separation on a C18 column, similar to step 1000, to remove the α-methyl mannopyranoside. However, a smaller C18 column (Waters C$_{18}$ Sep-Pak, 1 ml vol., Millipore Corp. of Milford, Mass; cat. #WAT051910) is sufficient with the more purified sample at this stage. This step also serves to concentrate the active fraction. The column is prepared by passing 5–10 ml MeOH followed by 5–10 ml water over it before loading with the 50 ml of conA eluate. The column is then washed with 10–20 ml water, and the active fraction is eluted in a volume of about 2 ml MeOH. The sample may be evaporated to dryness and resuspended in a volume of about 150 μl of distilled water. The resulting extract is pale yellow to brown (indicative of little or no anthocyanins). A large part of the anthocyanins are lost in the cation column separation.

Optionally, a step of extracting the aqueous sample with an equal volume of a moderately polar organic solvent, e.g., 50:50 CHCl$_3$/EtAc, may be introduced into the procedure of FIG. 10. This step is performed to remove some nonpolar or less polar compounds from the extract. CHCl$_3$-EtAc extraction may be performed either after step 1004, or prior to steps 1000, 1002, e.g. on the initial aqueous extract.

The CHCl$_3$-EtAc extraction appears to remove a component of the extract which masks or otherwise interferes with the activity of the anti-adhesion fraction in the RBC assay, since its removal generally enhances the activity as measured in that assay without significantly changing the mass yield. However, removal of the apparent "masking" component(s) may decrease the long-term stability of the active compound. Thus, the step of CHCl$_3$/EtAc extraction may be employed when attempting to quantitate anti-adhesion activity in the RBC assay, but it may be undesirable to include this step in routine production of the extract.

In performing the CHCl$_3$/EtAc extraction, the aqueous sample is preferably extracted twice (each time with an equal volume of CHCl$_3$/EtAc). The organic phase(s) are discarded, and the aqueous phase is concentrated by evaporation to about ⅓ its original volume (e.g., about 5 ml). The evaporation also removes trace amounts of the organic solvents. Alternatively, the sample can be evaporated to dryness and resuspended in water. Either way, the resulting aqueous sample is then further purified by step 1008 or step 1004.

Table VIII shows the relative adhesion-inhibiting activity measured for extracts at selected stages in the process of FIGS. 1 and 10, as measured in the red blood cell agglutination assay (abbreviated RBC assay; see EXAMPLE 2 and Table VI). The activity values are normalized to the activity of a 1% mannose solution in the assay and to the amount of material in g/ml. The mannose solution is 1% or 1 g/100 ml, so a value of 100 indicates activity equivalent to mannose. Values>100 indicate that the sample is more effective than mannose in anti-adhesion activity. The concentrations of the test extracts were determined by weighing portions evaporated to dryness.

The results shown in Table VIII demonstrate that (in general) different methods of producing the initial extract were comparable with the MeOH:HOAC:water ("MAW"). Water (room temperature) and boiling water extracts were slightly better in terms of recovery of activity. A 10% solution of OCEAN SPRAY™ powder was comparable to these as well. To estimate the amount of activity remaining in the pulp, the pulp was extracted with MeOH and the MeOH-soluble material was prepared in aqueous form.

The MAW extract is preferred, as it appears to result in a greater recovery of activity in the initial extraction from berries and to leave a smaller proportion of activity in the pulp.

Figure 13:
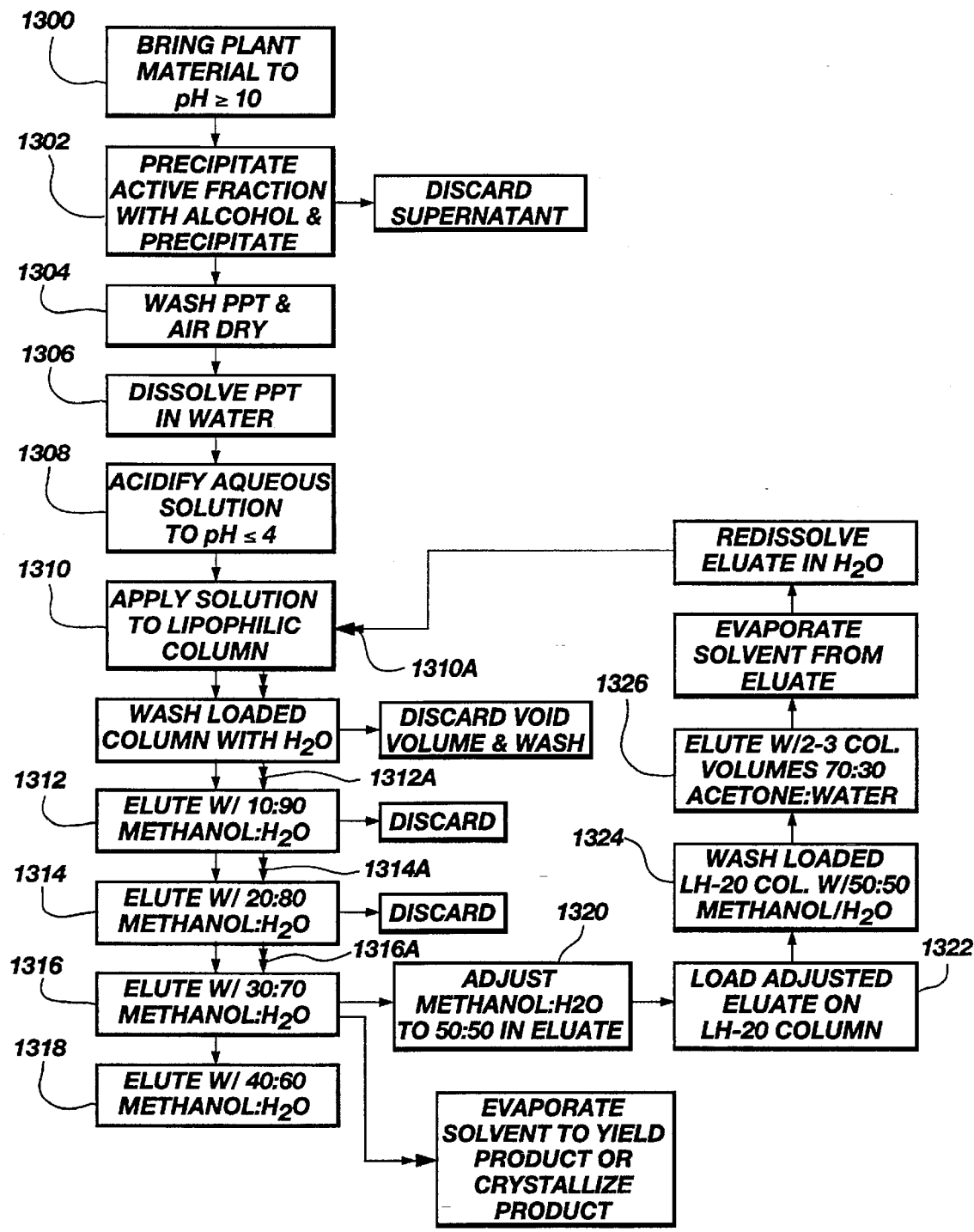
FIG. 13 is a flow chart of an alternate method of extract preparation.

An alternate procedure for preparing a cranberry extract having anti-adhesion activity, and further including steps of substantially purifying an active compound from the extract, begins with an alkaline pH adjustment of an anaqueous solution of previously extracted plant material in which the "active" compounds are soluble. As applied to an aqueous solution of OCEAN SPRAY™ cranberry powder ("OSCP solution"), the method went as follows. A sufficient amount of a strong base (e.g., NaOH) is added to the OSCP solution to bring it to a pH sufficient to ionize phenol groups of polyphenols to phenoxide groups, ($\geq$pH 10) (FIG. 13; step 1300). When the process was applied to the OSCP solution, the solution turned green upon reaching the necessary pH. For 1 liter of a saturated (20%) OSCP solution of cranberry powder, about 70–80 ml of 10N NaOH was used. The green, basic OSCP solution thus produced was then stirred with a sufficient amount of a simple alcohol to cause formation of a green precipitate (step 1302). About 4 volumes (4 liters) of MeOH were used. In place of MeOH, other 1 to 3 carbon alcohols miscible in water could have been used. The precipitate was allowed to settle, collected on filter paper, and then washed with a small volume (about ⅕ to ⅓ liter in the example) of "basic" MeOH (step 1304). "Basic" MeOH is MeOH alkalinized with about 1–2 ml of 10N NaOH per liter. The washed solids were air-dried, and the resulting light green powder, which contained increased levels of the active fraction as revealed by testing in the hereinafter described RBC agglutination assay, was stable for many months at room temperature. Most of the sugars were removed in this step. Generally, between about 70 and 80 grams of green powder were recovered per liter of 20% OSCP.

Next, a sufficient amount of the green powder was dissolved in 200 ml of water to make a strong or nearly-saturated solution (step 1306; generally 30–40 grams from the 20% OSCP process). The aqueous solution was then acidified to convert the phenoxide ions back to phenol groups, in the present case, by adding sufficient concentrated acid (e.g., about 13–16 ml of 12M HCl) to bring it to a pH between about 3 and 4 (step 1308). In the case of extraction from OSCP, the solution turned to a wine-red color upon reaching the appropriate pH. Undissolved solids were removed (e.g., by filtration or centrifugation), and the supernatant solution was applied to a C18 lipophilic column (Waters Cartridge) which had been preconditioned with MeOH and then washed with deionized water (step 1310). After the cranberry-derived solution had been loaded, the C18 column was washed with 2–3 column volumes of water and eluted in step-wise fashion with MeOH:H$_2$O mixtures of varying proportion. For a 35 ml C18 column having about 200 ml of the acidified cranberry-derived solution loaded thereon, elution step 1312 was with 100 ml (2–3 column volumes) of a mixture of 10:90 MeOH/H$_2$O (vol./vol.), elution step 1314 was with 100 ml of 20:80 MeOH/H$_2$O, elution step 1316 was with 100 of 30:70 MeOH/H$_2$O, and elution step 1318 was with 100 of 40:60 MeOH/H$_2$O. Other water-miscible alcohols could have been substituted for MeOH, with appropriate adjustment to the alcohol:water proportions to achieve the desired separation. Also, other non-polar organic solvents in comparison to water (e.g., acetonitrile) could have been substituted for the alcohol. Further, other similar reverse-phase silica gel columns, such as C2 or C8 or phenyl or the like columns, may have been substituted for C18 or lipophilic SEPHADOX™ LH-20 or LH-60 or the like.

The eluate of step 1316 was highly enriched for anti-adhesion activity, and included the procyanidins and flavanoids. To further purify the procyanidin, the step 1316 eluant was brought to 50% MeOH (step 1320), either by evaporation and redissolution or by adding MeOH. This solution was then applied to a hydroxypropylated gel filtration column (e.g. LH-20 SEPHADEX™ column, available from Sigma Chemicals), which had been pre-conditioned with 50:50 MeOH/H$_2$O (step 1322). The column volume should generally be about 1/10 to about ½ of the starting volume of the acidified solution. After loading the 50:50 MeOH-adjusted solution of the eluate on the LH-20 column, the column was washed with 50:50 MeOH/H$_2$O (step 1324). The LH-20 column was then eluted with about 2–3 column volumes of 70% acetone in water (vol./vol.) (step 1326): the eluate evaporated to dryness and re, dissolved in water. The LH-20 column selectively separated catechins, procyanidin polymers, and perhaps other polyphenols absorbing at 280 nm, from other polyphenolic compounds. To achieve a similar separation, a phenyl-SEPHAROSE™ column or an LH-60 column (Sigma Chemical Co. of St. Louis, Mo.) could have been substituted for the LH-20 . Both LH-20 and LH-60 SEPHADEX™ comprise hydroxypropyl groups pendant via ether linkages from SEPHADEX™ beads, making the SEPHADEX™ material more lipophilic.

The LH-20 eluate redissolved in water (in neutral form, or preferably acidified as in step 1308) was then applied to another C18 lipophilic column similar to that used in step 1310, and subjected to the same step-wise elution protocol (steps 1310A, 1312A, 1314A, 1316A). The eluate from step 1316A (30% MeOH eluant) contains substantially a single compound absorbing at 280 nm, eluting at 18–19 minutes in the analytical HPLC procedure outlined in FIG. 14D. Generally, between about 0.03 and about 0.10 grams of the purified compound are recovered from 1 liter of the 20% OSCP, that is, a recovery of about 0.01% to about 0.05%. This recovery, of a single active compound is at least 20-fold the recovery of mixed active compounds achieved by the methods described previously herein.

B. The Extracts:

Table I shows the solubility of one embodiment (cranberry powder) of the invention in various solvents of differing degrees of polarity.

The refractive index of an aqueous solution of the powder is about 1.3320 at a concentration of 1.0 mg/ml, and about 1.3370 at a concentration of 8.5 mg/ml (the maximum solubility in water).

TABLE I

| Solvent | Solubility |
| --- | --- |
| Acetone | 133 mg/ml |
| Methanol | 530 mg/ml |
| Ethanol | 450 mg/ml |
| Butanol | 275 mg/ml |
| Water | 8.5 mg/ml |

Figure 2:
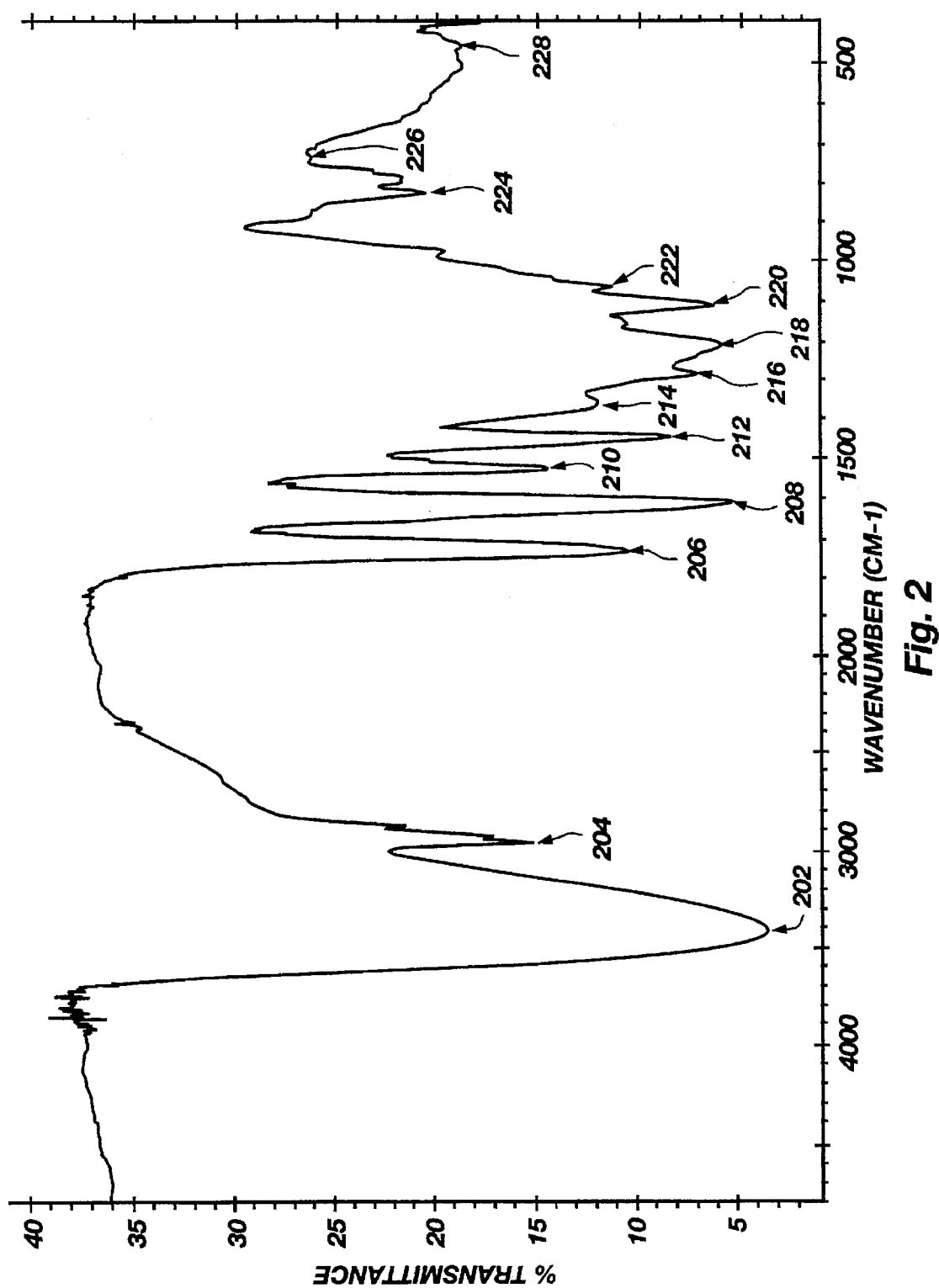
FIG. 2 is an infrared ("IR") absorbance spectrum (KBr solid) of the extract.

The extract prepared from cranberries (berries of *V. macrocarpon*) has certain characteristics observable in absorbance spectra in the infrared, visible and ultraviolet light ranges. FIG. 2 shows an IR transmittance spectrum of the extract, with significant absorbance troughs at approximately the following respective wave numbers in $cm^{-1}$: 3410, 2960, 1735, 1610, 1524, 1443, 1360, 1285, 1210, 1111, 1066, 822, 785, 500, which are respectively indicated by reference numerals 202, 204, 206, 208, 210, 212, 214, 216, 218, 220, 222, 224, 226, 228. Peak 228 at about 500 $cm^{-1}$ is very broad.

Figure 3:
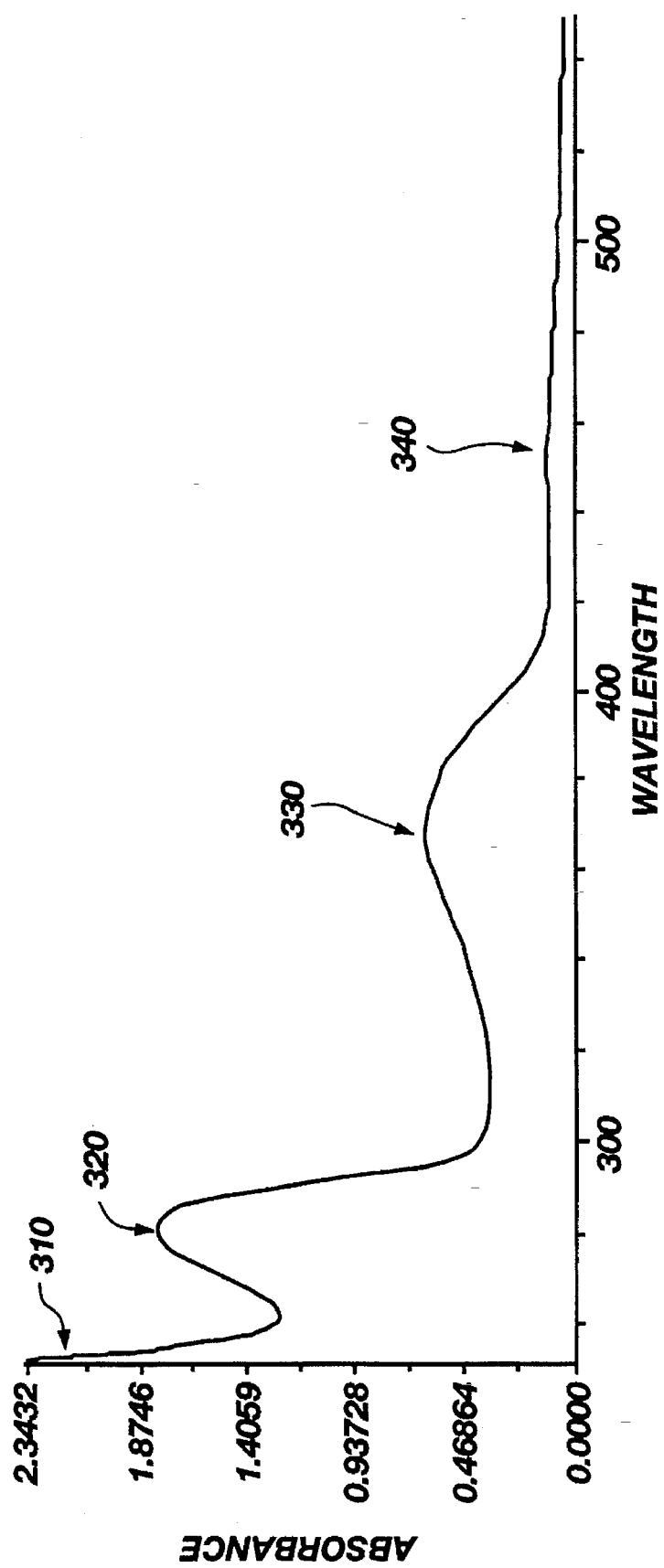
FIG. 3 is an ultra-violet ("UV")/visible light absorbance spectrum of the extract dissolved in methanol.

FIG. 3 shows an absorption spectrum of the cranberry extract dissolved in MeOH, for wavelengths from about 250 nm through about 600 nm (the UV and visible light regions). The concentration of the extract in MeOH is about 0.05 mg/ml. Four major absorption maxima are observed between about 200–500 nm with peaks usually at 200–210 nm, and 275–290 nm, and 355–375 nm, and 440 to 460 nm. These maxima are indicated by arrows 310, 320, 330, 340. These four peaks appear to be characteristic of the extract. The relative intensities of the peaks may be somewhat variable, but are generally in the range of about 1.8:0.64:0.12 respectively for the peaks 320, 330, 340. Polyphenols, including flavonoid-containing compounds, are known to have UV/visible light-absorbance spectra with similar features. The cranberry extract also exhibits strong fluorescence at 315 nm when excited at 280 nm light. Both fluorescence and absorptions spectral maxima are shifted to the red by the addition of $AlCl_3$, which is characteristic for phenolic compounds.

Figure 4:
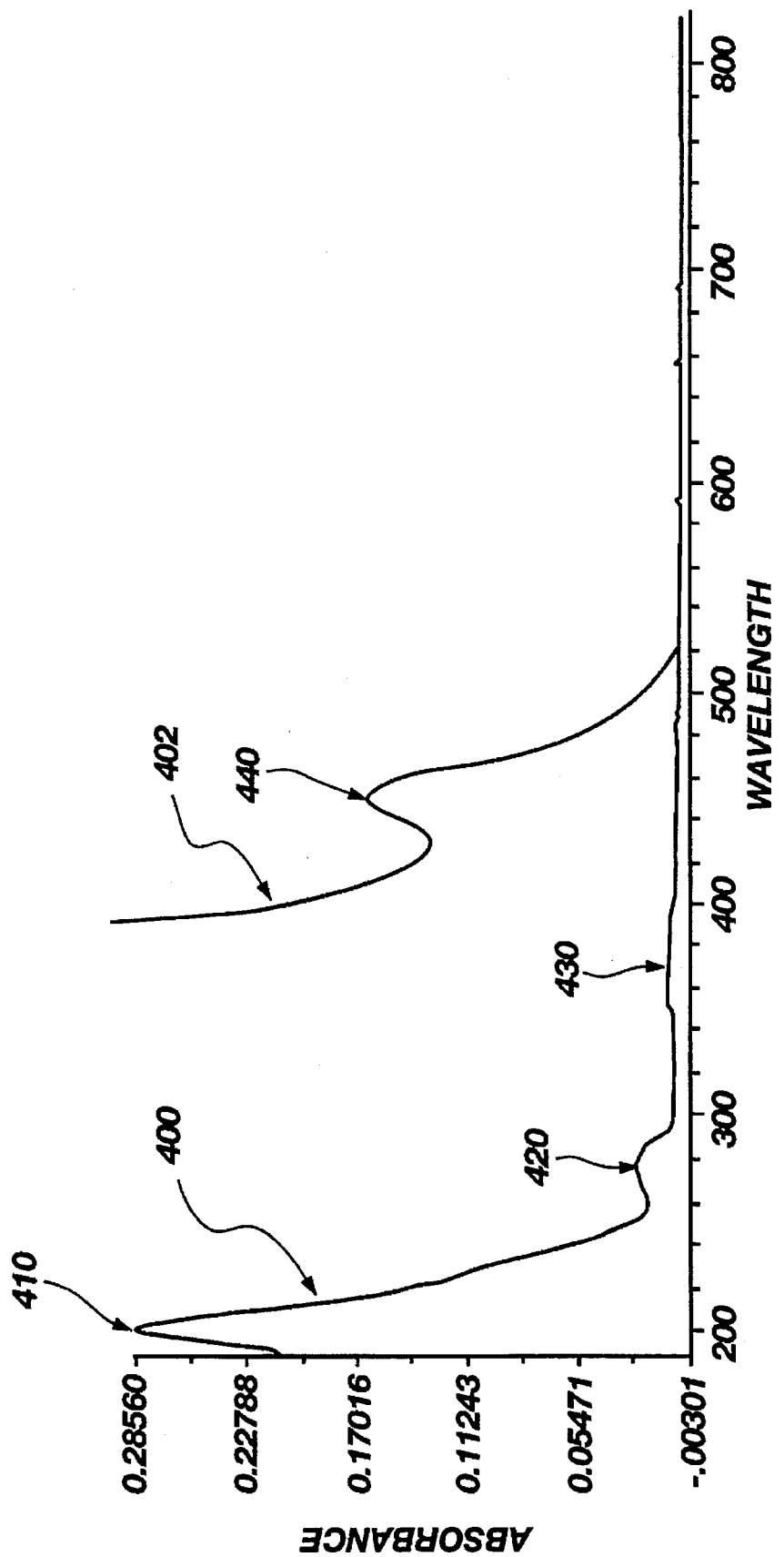
FIG. 4 is an UV/visible light absorption spectrum of the extract dissolved in water.

FIG. 4 depicts absorption spectra of the cranberry extract dissolved in water, at two different concentration levels (curves 400, 402). Curve 402 is taken from a sample which is 200 times more concentrated than that of curve 400. The spectrum has the following characteristic absorbance peaks: 202, 278, 368, and 454 nm, which are indicated respectively by reference numerals 410, 420, 430 and 440. The approximate relative intensities of the peaks are, in $(mg/ml)^{-1}(cm)^{-1}$, 0.28, 0.025, 0.0031, and 0.00085, respectively. Peak nos. 420, 430 (278 nm and 368 nm, respectively) are also characteristic of the spectra in water of flavonoid- and polyphenol-containing compounds. Generally, an absorbance at both 280 nm and 360–370 nm is indicative of the presence of flavonoids, whereas polyphenols have the greatest absorbance in the 200 nm to 280 nm range and exhibit little or no absorbance at 360–370 nm.

The flavonoid/polyphenol compounds present in the extract include compounds having a glycoside moiety. Several flavonoid compounds lacking a sulfate or pyranoside (e.g., glucuronide) moiety, including myricetin, rutin, and quercetin, were tested and found not to have anti-adhesion activity.

Figure 5A:
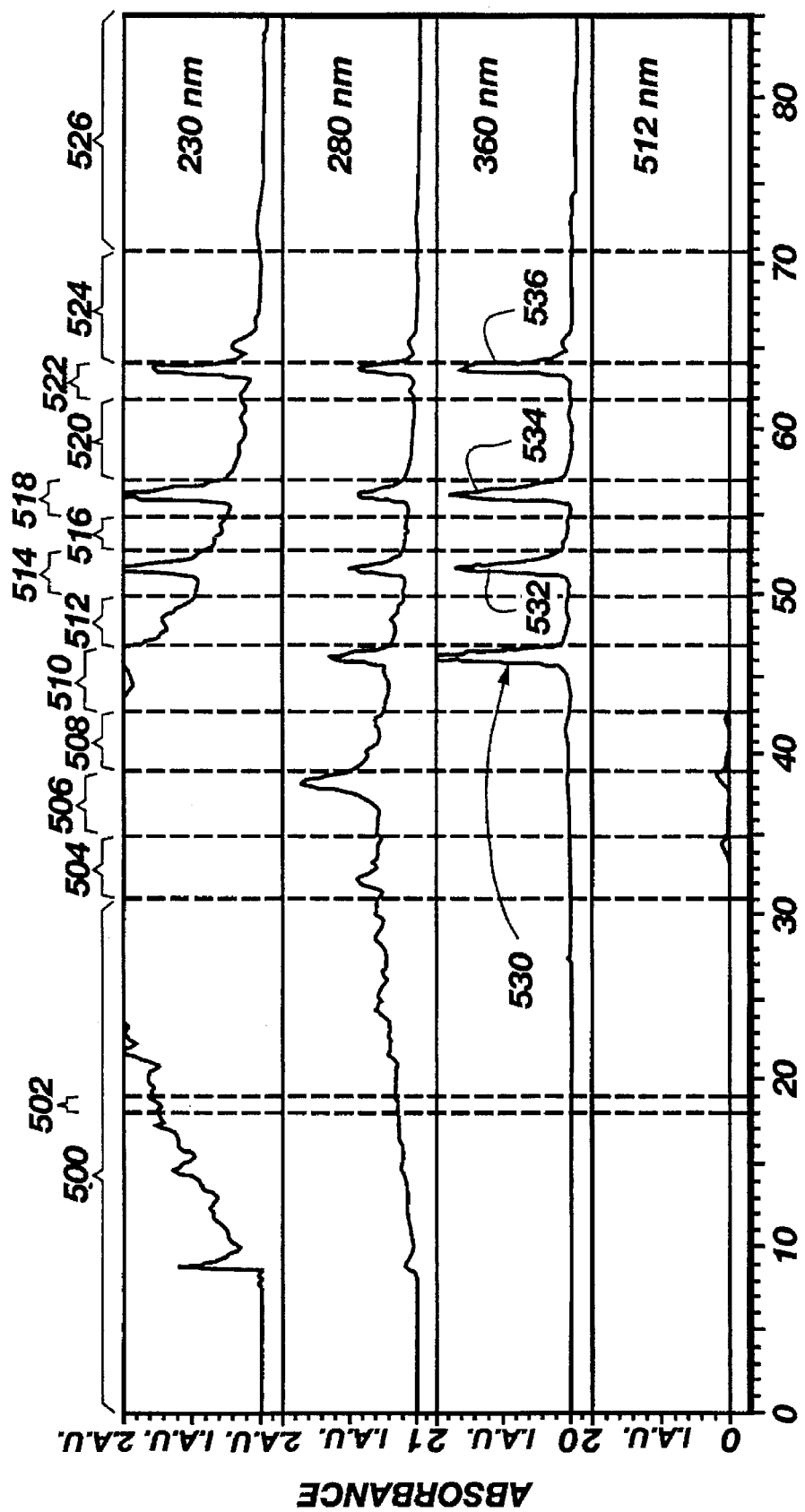
FIGS. 5A–5B depict a comparative analysis of a high-pressure liquid chromatogram of the extract by absorbance at wavelength of 230 nm, 280 nm, 360 nm and 512 nm.
Figure 6B:
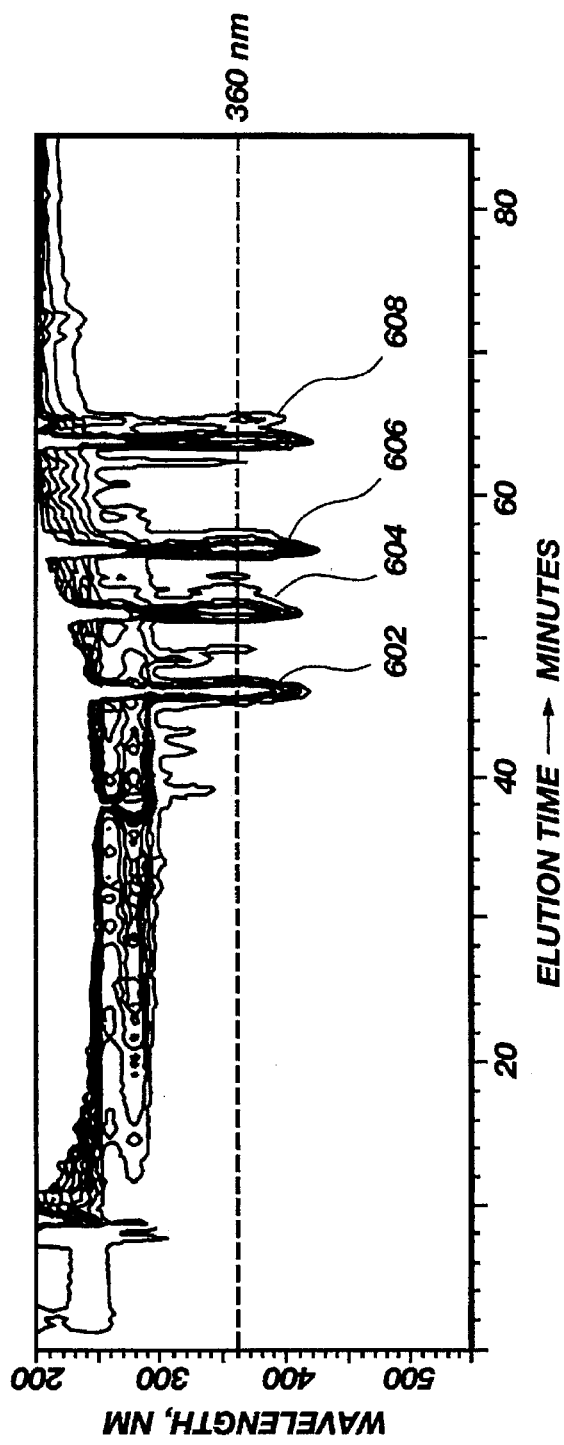
FIGS. 6A–6B are charts depicting a dual spectral analysis and analysis of elution peaks absorbing at 360 nm of a high-pressure liquid chromatogram of the extract.
Figure 6A:
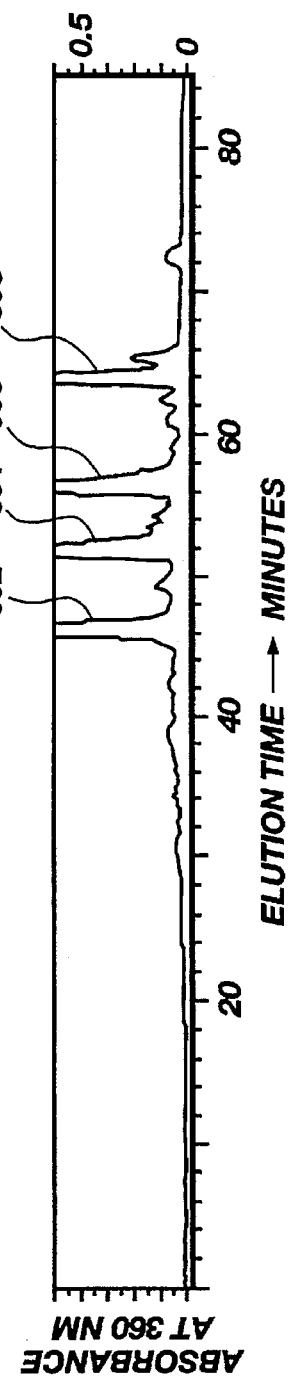
Figure 7A:
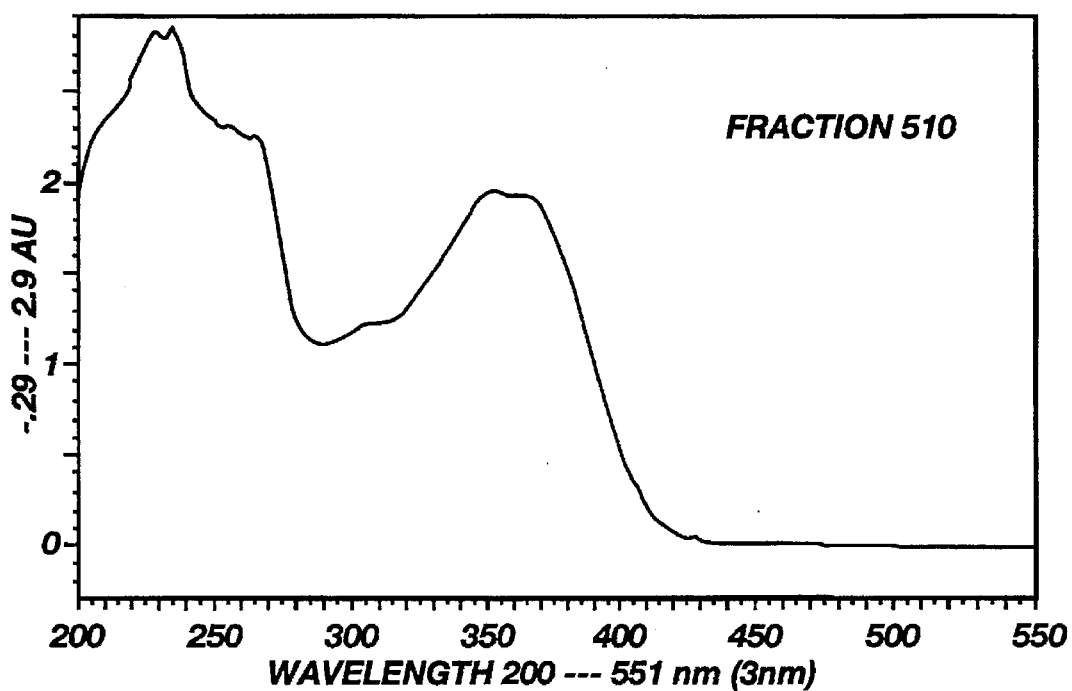
FIGS. 7A–7F are charts depicting the complete UV-visible light spectra of selected high-pressure liquid chromatography ("HPLC") fractions taken from the sample, which chromatogram is shown in FIGS. 5A–5B.
Figure 7B:
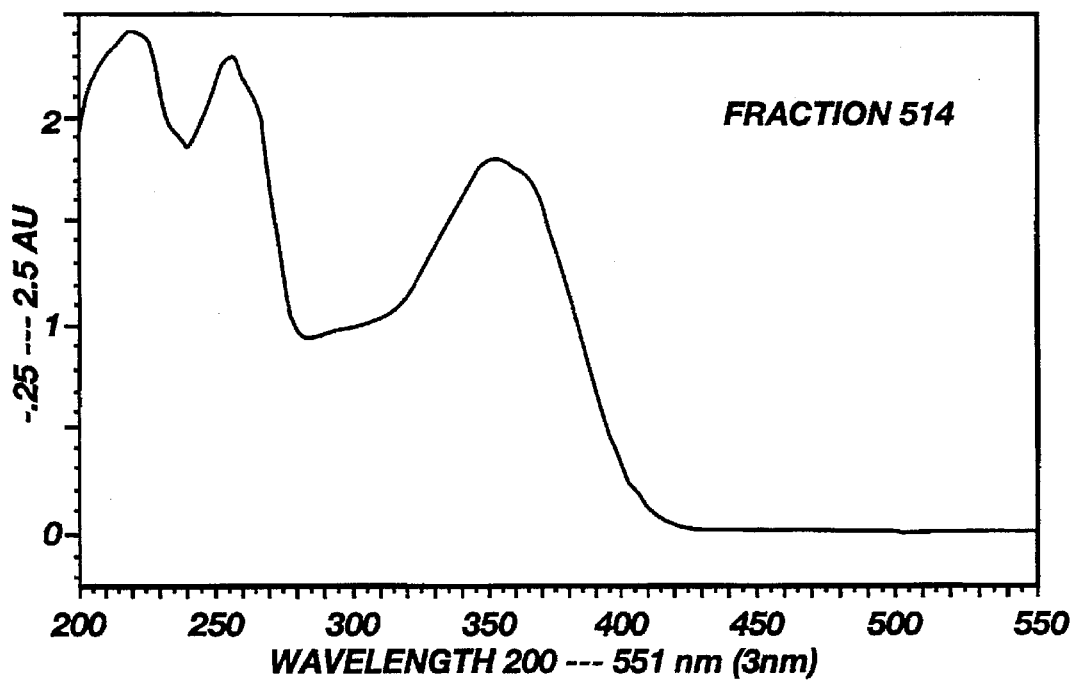
Figure 7C:
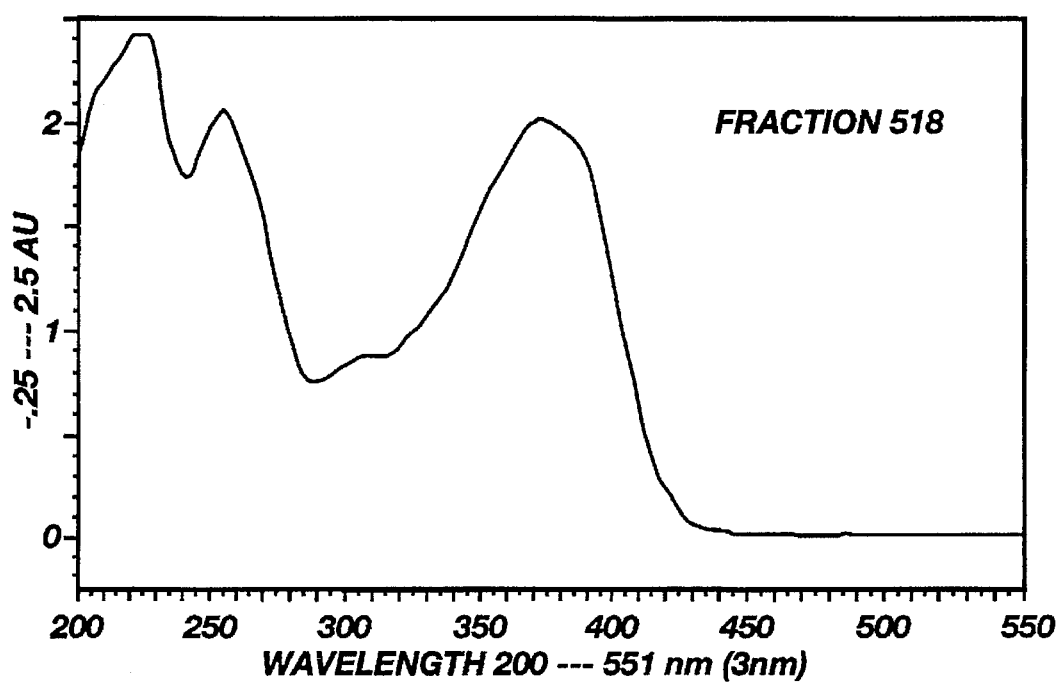
Figure 7D:
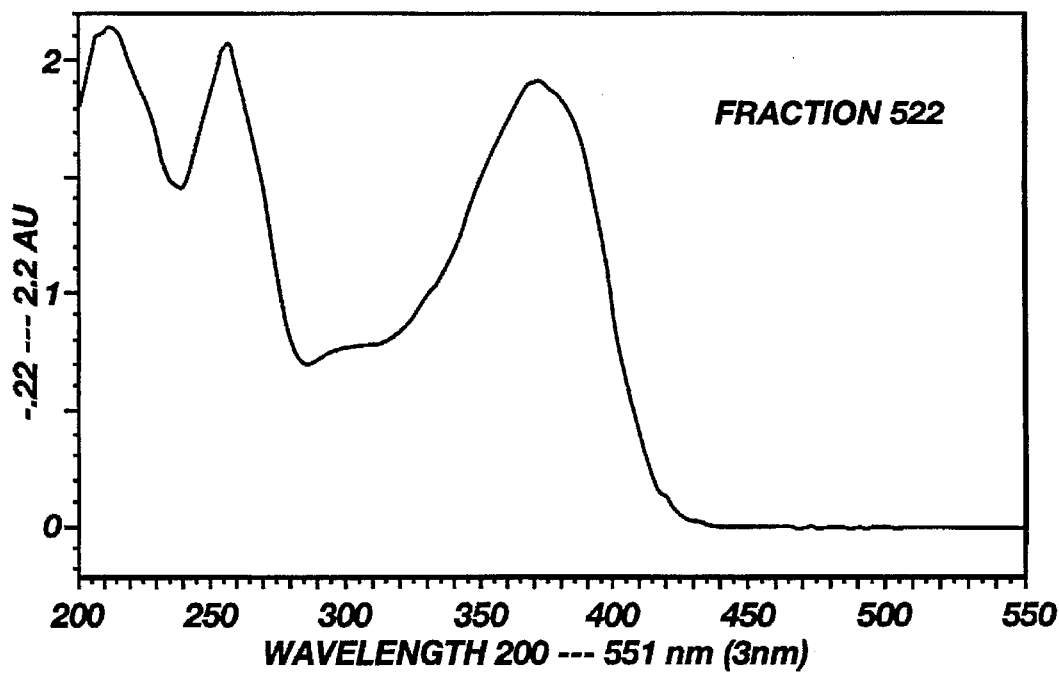
Figure 7E:
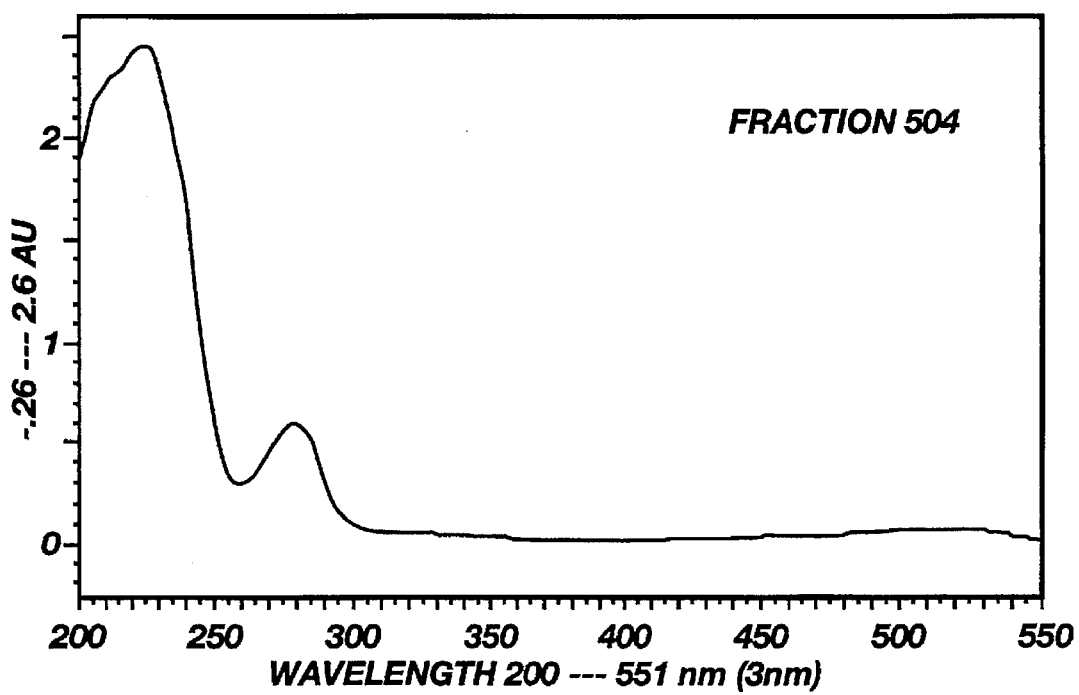
Figure 7F:
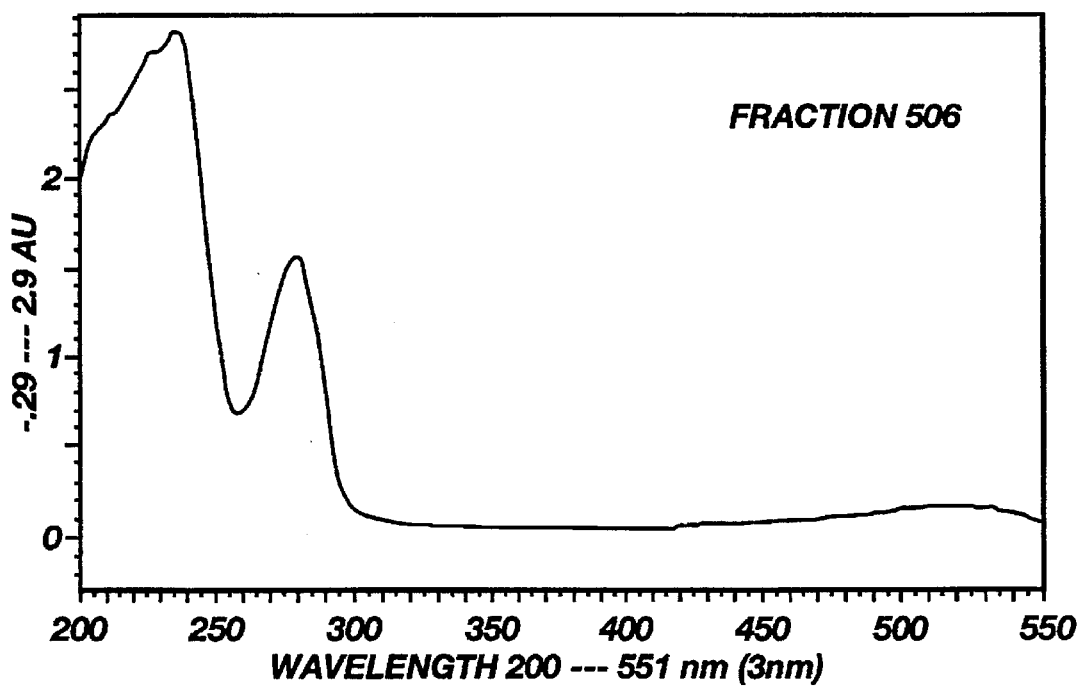

The cranberry extract is also characterized by the elution at specific times during HPLC of the extract dissolved in MeOH, of 360 nm light-absorbing components. FIGS. 5A and 6A depict typical elution vs. time chromatograms of the cranberry extract of components that absorb at 360 nm. Fifteen hundred μl of a solution containing 100 mg of dry powder per 4 ml of MeOH (i.e., about 37.5 mg) was applied to a preparative-size, reverse phase C18 column (Waters C18 prepacked column, BONDAPAK, cat. #WAT038505, Millipore Corp., of Milford Mass., USA). C18 is a lipophilic affinity agent having carbon chains 18 carbons in length bound to the beads. For a preparative size column of about 50 ml volume, 25 mm diameter and 100 mm length, a two-solvent linear gradient from 80% A/20% B (A=0.4% phosphoric acid, B=MeOH) to 31% A/69% B is run at a flow rate of 5 ml/min. over a time from 0 to 76 min. After 76 min., an isocratic flow at 31% A/69% B is maintained for an additional 44 min. With photodetection at 360 nm, about four large 360 nm-absorbing peaks are observed respectively at about 46, 52, 56 and 64 min. (identified by reference numerals 602, 604, 606, 608, respectively, in FIGS. 6A & 6B).

For an analytical column of about 5 ml volume (FIG. 8), about 1.25 mg powder is loaded in a volume of about 1 ml water or alcohol. A two-solvent linear gradient from 80% A/20% B (A=0.4% $H_3PO_4$, B=MeOH) to 31% A/69% B is run at a flow rate of 1 ml/min. over a time from 0 to 38.3 min. After 38.3 min., an isocratic flow at 31% A/69% B was maintained for an additional 21.7 min. With photodetection at 360 nm, about four major elution peaks are observed at elution times between about 22 min. and about 40 min., and three smaller elution peaks appear earlier, at between about 9 min. and about 15 min. Alternatively, a revised method to improve base line noise and improve peak symmetry is used for FIGS. 14A–14D. A two-solvent linear gradient from 79% A/21% B (A=0.4% phosphoric acid, B=95% MeOH and 5% 0.4% phosphoric acid) to 35% A/65% B is run at a flow rate of 1 mL/min. over a time from 0 to 38.3 min. After 38.3 min., an isocratic flow at 35% A/65% B was maintained for an additional 21.7 min. The column is then washed with 100% MeOH for an additional 10 min. at a flow rate of 1.0 mL/min. Purified substances used for calibration are catechin (8.4 min.) epicatechin (14 min.), and quercetin (36 min.). One of the most active substances that occurs naturally in cranberry elutes at 19 min.

In some cases (e.g., FIG. 9), a 50 ml preparative column was first run for five min. at 80% A, followed by the linear gradient from 80% A to 31% A over the next 38.3 min., and finally by an isocratic phase at 31% A for the succeeding 21.7 min. (total time 70 min.). With this gradient protocol, the pattern of 360 nm-absorbing elution peaks associated with the active fraction of the extract is somewhat different, but closer to that observed for the analytical column.

The cranberry extract is also characterized by certain UV-fluorescing components migrating in a specific pattern in paper and thin-layer chromatography ("TLC"). When a solution of the cranberry extract is subjected to TLC on silica gel in a 98:2 acetone:water solvent, four characteristic fluorescing bands may be observed under long-wave ultraviolet light. These characteristic bands have the properties as described in Table II:

TABLE II

Relative migration distance ($R_f$) and color upon irradiation with UV light for characteristic bands observed by TLC in acetone:water (98:2).

| | Rf | Color |
|---|---|---|
| Band #0 | 0.0 | faint red |
| Band #1 | 0.2 | blue/blue-white |
| Band #2 | 0.6 | bright yellow |
| Band #3 | 0.7 | bright yellow |
| Band #4 | 0.97 | white |

When subjected to paper chromatography on a Whatman #3 paper with a solvent system of 6:1:2 butanol:HOAc:$H_2O$, three significant fluorescent peaks are observed on exposure to long-wave (366 nm) UV light. These three peaks are described in Table III:

TABLE III

Relative migration distance (Rf) and color of fluorescent bands observed upon irradiation with long-wave UV light, for paper chromatography in 6:1:2 butanol:acetic acid:water.

| | Rf | Description |
|---|---|---|
| Band #5 | 0.44 | strong fluorescent yellow |
| Band #6 | 0.50 | faint fluorescent yellow |
| Band #7 | 0.77 | medium fluorescent yellow |

In a preferred embodiment, the enriched extract is substantially free of free simple sugars (monomer and dimer sugars such as fructose, galactose, glucose, sucrose, etc).

In one embodiment, the total acid content of the enriched extract (including benzoic acid) is less than about 2%. Benzoic acid is usually present at less than about 0.005 mg per gram. This benzoic acid content is less than or equal to about 1% of that found in certain existing products, as summarized in Table IV. Juice products were reduced to a powder before testing and the acid content is given in relation to the mass of the resulting solids. The reduced content of benzoic acid and total acid results in a product with a less sour taste and which is believed to be less likely to cause stomach upset or promote tooth decay.

TABLE IV

| Product | Wt. % Benzoic Acid |
|---|---|
| KNUDSEN ™ cranberry juice | 0.50 |
| HAINS ™ cranberry juice | 0.11 |
| JANET LEE ™ cranberry juice | 0.06 |
| OCEAN SPRAY ™ cranberry cocktail | 0.10 |
| OCEAN SPRAY ™ cranberry powder | 0.12 |
| Cranberry extract of application | 0.0002 |

The cranberry extract having the foregoing properties, including a very low content of simple sugars and benzoic acid, has been found to interfere with adherence of bacterial cells to certain cell types, as well as to surfaces such as polystyrene.

C. Uses:

A method of inhibiting the adhesion of bacteria to surfaces comprises the steps of providing a Vaccinium extract enriched for anti-adherence activity and for 280 nm-absorbing and/or 360 nm-absorbing polyphenol compounds, and applying an effective amount of a composition comprising the extract in an acceptable carrier to a surface believed to have bacteria such as *E. coli* adhered thereto to disengage the bacteria from the surface. Desirably, the surface is rinsed to remove the disengaged bacteria. The method is useful to inhibit the adhesion of bacteria to such surfaces as teeth, other bacteria adhered to teeth, human oral epithelial cells, and human epithelial urinary tract cells; and to clean dental implants, bacterial fermentation vats, and the like.

D. Compositions:

The invention includes oral hygiene products containing a Vaccinium-derived active ingredient, as disclosed previously herein, having microbial anti-adhesion properties. Such oral hygiene products include, but are not limited to, dentifrices, oral rinses, and chewing gums.

A dentifrice of the invention would be made by preparing an effective amount of the Vaccinium-derived "active ingredient" in a conventional powder or paste carrier, the carrier being comprised of ingredients including a hydrophilic base, emulsifiers, flavoring agents, fragrance agents, preservatives, etc., in conventional proportions. Such a dentifrice may include effective amounts of abrasive components for mechanical disruption/removal of tartar and/or fluoride. A specific example of a toothpaste includes the Vaccinium-derived active ingredient in an amount of between about 0.2% and about 5% by dry weight in combination with toothpaste constituents.

A chewing gum would contain a conventional gum component, a preservative, and an effective amount of the active ingredient. In the gum, the amount of the active ingredient will generally be between about 0.5% and about 5% by dry weight.

An oral rinse may contain an aqueous or aqueous-alcohol liquid carrier, a preservative, and an effective amount of the active ingredient, the latter being generally between about 0.5% up to about 10% by volume, or 0.005 to 2% by dry weight.

Another product in which the extract and/or novel compounds find use is a throat spray or lozenge to treat a sore throat by, for example, reducing or preventing adhesion of deleterious bacteria to throat tissues.

Conventionally, hydrogen peroxide or other strong oxidizing agents are sometimes included in oral hygiene products. However, at present it is believed preferable not to include strong oxidizing agents such as hydrogen peroxide, as these may cause unsaturation of the ring B in certain Vaccinium-derived active compounds and thereby destroy their anti-adhesion activity.

It is also contemplated that the Vaccinium-derived active ingredient may be prepared in capsule or tablet form for regular administration to help maintain urinary tract health, and particularly as a prophylactic against urinary tract infections. Or, beverages enriched for the active ingredient could be prepared for a like purpose, making the known benefits of cranberry juice available to individuals who dislike the taste of cranberries. The active ingredient should be present in an amount of from 5 to 500 mg in a tablet form, or in an amount to provide a similar dosage in a 100 ml to 250 ml beverage.

The Vaccinium-derived active ingredient could also be prepared in compositions for treatment of urinary tract infections. In tablet form, such a composition would include from about 10 to about 500 mg of the Vaccinium-derived ingredient per dose unit in a suitable inert carrier, with the dose to be taken 2–4 times daily. Optionally, one or more of the following may be included: phenazopyridine HCl for relief of acute symptoms (from about 50 mg to about 200 mg per dose unit); methenamine as an anti-infective agent (from about 50 mg to about 500 mg methenamine per dose unit); and a urinary acidifier such as sodium diphosphate, hippuric acid, ascorbic acid, or mandelic acid (from about 100 mg to about 500 mg per unit dose).

A foot powder according to the invention would typically include an effective concentration of the extract admixed with miconazole or clotrimazole, talc, starch, and possibly fragrance. When incorporated into an aerosol, a propellant would also be used.

A foot ointment or cream would typically include an effective amount of the extract, miconazole or clotrimazole, petroleum, lanolin, sodium lauryl sulfate, emulsifiers, and preservatives.

A foot solution would typically include the inventive extract, an antifungal such as miconazole or clotrimazole, and a solvent system (e.g., water and alcohol).

A vaginal cream for treating yeast infections would include the extract, an effective amount of an antifungal such as clotrimazole, miconazole or terconazole, benzyl alcohol, cetyl alcohol, and wax or other cream base.

Examples

EXAMPLES 1–3 demonstrate the anti-adherence properties of the extract. At least three modes of bacterial cell adherence to other cells and surfaces are known. One mode is mediated by type 1 pili on the surface of the bacteria, and is characterized by sensitivity to free mannose. A second mode is mediated by P-type pili ("P-type fimbriae"). The mechanisms of the third mode and other adherence modes are not well-characterized. Guinea pig erythrocytes are believed to have receptors for the type 1 (mannose-sensitive) pili of *E. coli*, since the bacteria are capable of agglutinating guinea pig erythrocytes in the absence of mannose but not in its presence (see, e.g., Aronsen, *J. Infect. Dis.* 139:329–332 (1979); Riegman, *J. Bacter.* 172:1114–1120 (1990); Jann, *Infect. Immun.* 22:247–254 (1981)).

Example #1

Anti-adherence activity measured as interference with bacterial adherence to bladder cells:

Human bladder epithelial cells were collected by centrifugation from the urine of a healthy female volunteer. The cells were washed in standard saline citrate (SSC) and resuspended to the desired volume. The optical density of the cell solution and cell counts were determined. *E. coli* bacterial strains isolated from urinary tract infections were cultured in tryptic soy broth at 37° C. for 72 hours to encourage piliation. The bacteria were also harvested by centrifugation, resuspended in the desired volume of SSC, and the approximate cell number determined.

A test tube was prepared containing 0.667 ml of a selected dilution of the substance to be tested for anti-adherence activity, plus 0.334 ml of the bacterial suspension. The bacteria were incubated with the test substance (an enriched extract produced from cranberries by the process of FIG. 1, Step 116) for 15 min. at 37° C. Next, 1.0 ml of the bladder cell suspension was added to each tube and the tubes were incubated for a further 15 min. Cranberry extract was used in an 8.5 mg/ml solution. Unfractionated cranberry juice was also tested.

After incubation, the content of each tube was filtered through an 8 micron polycarbonate filter, and the filter was rinsed with two volumes (2 ml=one volume) of SSC to wash free any bacteria that were not adhered to the bladder cells. The falter was placed face down on a microscope and the cells were heat-fixed to the slide. The filter was removed, the slides were stained to visualize the cells, and the number of bacteria adhering per cell was counted for each of 20 cells per slide.

Two control tests were also performed. First, the bladder cells were incubated only in SSC without any bacterial suspension or test substance to determine how many bacteria originating in the urine sample were attached to the epithelial cells. Second, SSC was substituted for the test substance to determine the maximum number of bacteria that adhered to the cells without any inhibitor.

Example #2

The following test was developed and used to test the ability of the extract to inhibit agglutination of guinea pig red blood cells ("RBC") by *E. coli*:

RBC, from guinea pigs (Microbio Products of Tempe, Ariz.) as a suspension in Alsevers solution, were washed in SSC and resuspended in SSC. Human RBC, obtained by standard methods from the blood of volunteers, were prepared by washing and resuspending in SSC. Human RBC are believed to have a receptor for mannose-resistant pili of *E. coli*.

*E. coli*, cultured and prepared as described in EXAMPLE 1, were tested as follows. A series of dots containing graded amounts of the test substance diluted in SSC, plus one dot containing SSC only, were placed on a polystyrene plate. The dots had a volume of about 10 µl. An equal volume of bacterial suspension was mixed into each dot, followed by ½ volume of RBC. The total volume in each dot, for a starting volume of 10 µl per dot, was thus 25 µl. The contents of each dot were thoroughly mixed and the degree of agglutination was scored on a scale of 0–4, with 0 representing no agglutination. The sum of the dot scores for all dilutions was totalled and subtracted from 32 to provide an Activity Index of activity interfering with agglutination.

Figure 5B:
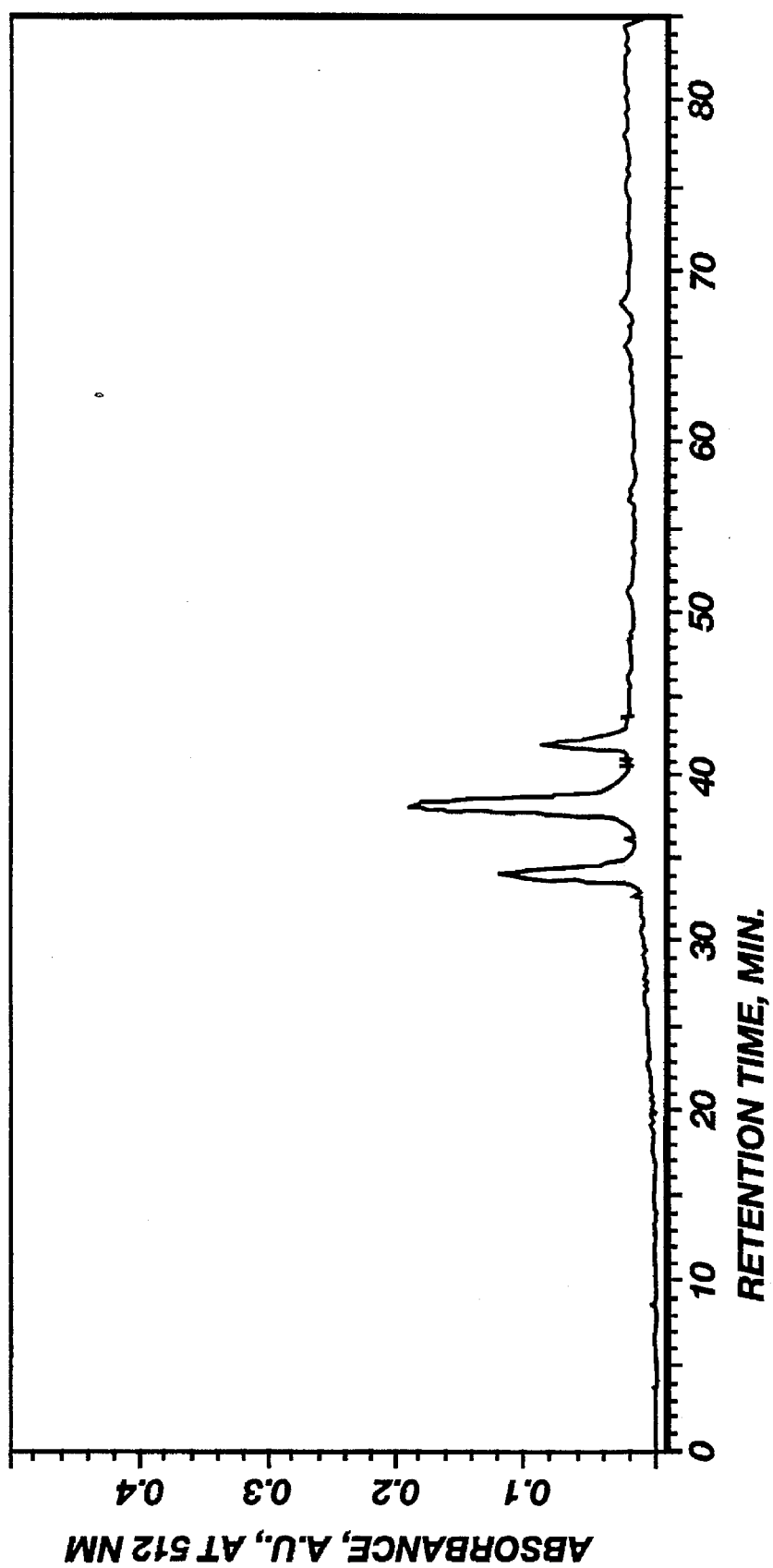

FIGS. 5A, 5B and 6A, 6B depict absorbance chromatograms from high-pressure liquid chromatography (preparative-type column. 25 ml by 100 ml). In FIG. 5A, absorbance at four different wavelengths is shown: 230, 280, 360, and 512 nm. Flavonoids and polyphenols are known to have significant absorbance at about 280 nm, with flavonoids also having an absorbance peak at about 360 nm. Anthocyanins are known to have significant absorbance of 512 nm Light. FIG. 5B is a magnified duplicate of the chromatogram at 512 nm of FIG. 5A. From a comparison of FIGS. 5A and 5B, it can be seen that the peak heights of peaks corresponding to anthocyanin absorbance are about 1/10 or less than the peak heights of peaks corresponding to polyphenol absorbance (280 nm).

Twelve fractions 502, 504, 506, 508, 510, 512, 514, 516, 518, 520, 522, 524 were separately collected and further analyzed. Fractions 510, 514, 518, 522 contained significant peaks absorbing at about 350 to about 370 nm, wavelengths characteristic of flavonoid and polyphenol moieties. Fractions 504 and 506 spanned the retention time of anthocyanin peaks, absorbing at 512 nm.

Figure 9:
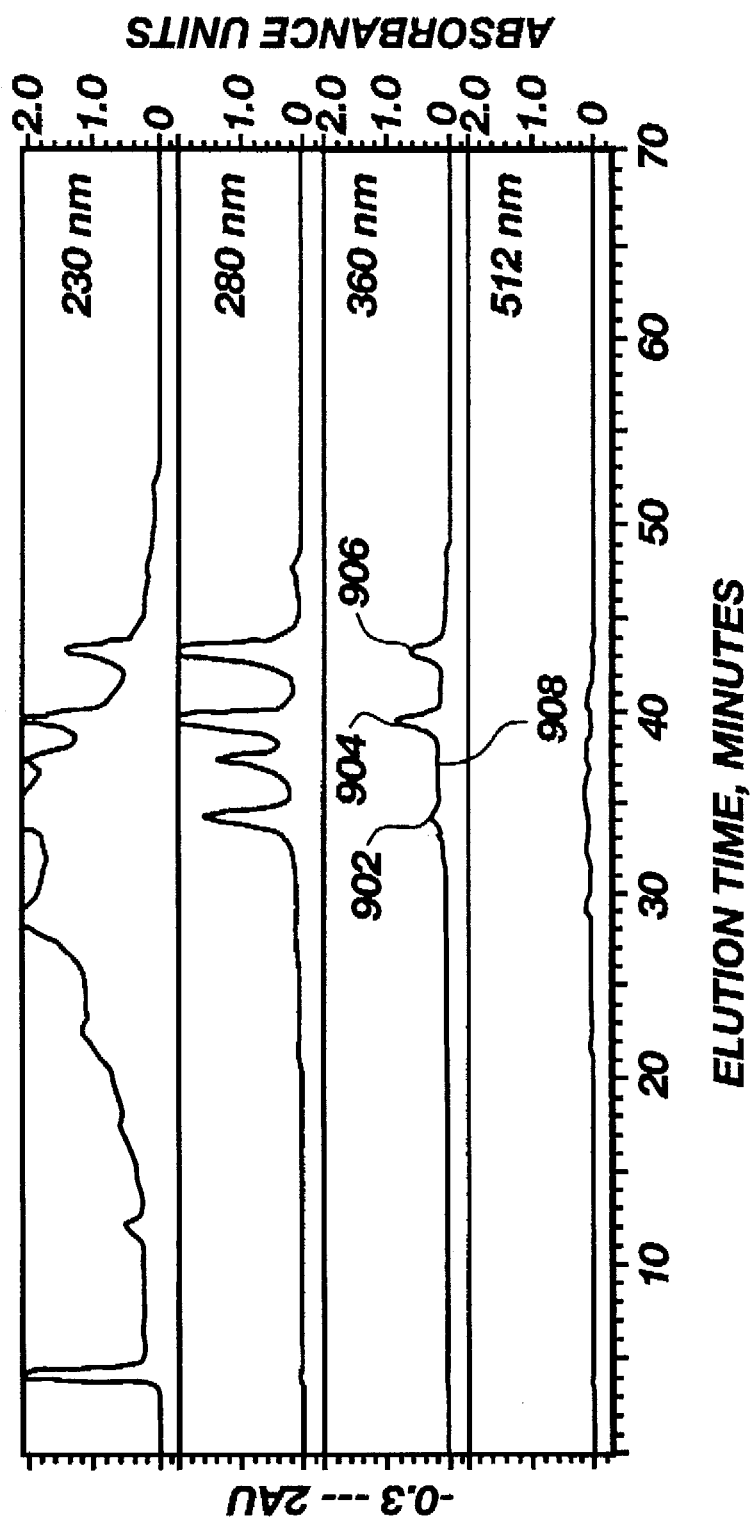
FIG. 9 depicts a chromatogram of the extract obtained with a different elution gradient than the chromatograms of FIGS. 5A–5B and 6A–6B.

Table V compares the anti-adherence activity of the fractions 502 through 524 with that of a whole (unfractionated) extract. A chromatogram of the latter sample is depicted in FIG. 9 (obtained by the alternative gradient procedure with 50 ml size column). Charts of the absorbance spectrum of fractions 510, 514, 518, 522, 504, and 506 are depicted in FIGS. 7A–7F, respectively.

From these spectra, it is apparent that fractions 510, 514, 518 and 522 all contained relatively large quantities of material absorbing at about 350–360 nm. Additionally, as seen in Table V, substantial anti-adhesion activity was found in fractions 504, 506, which did not contain detectable amounts of 360 nm-absorbing material. Fractions 504, 506 contain small amounts of compounds absorbing at 512 nm (which are believed to be anthocyanins), and substantial amounts of material absorbing at 230 to 280 nm. However, a cranberry anthocyanin preparation was analyzed and found not to contain detectible anti-adhesion activity (see Table VI). Thus, it appears that at least some of the cranberry anti-adhesion activity is found in some compounds absorbing at 230 to 280 nm.

TABLE V

Comparison of HPLC Fractions in Guinea Pig RBC Agglutination Assay

| Fraction # | Activity Index |
|---|---|
| 510 | 6 |
| 512 | 4 |
| 514 | 5 |
| 516 | 2 |

TABLE V-continued

Comparison of HPLC Fractions in Guinea Pig RBC Agglutination Assay

| Fraction # | Activity Index |
|---|---|
| 518 | 1 |
| 520 | 0 |
| 522 | 0 |
| 524 | 0 |
| 526 | 4 |
| 504 | 18 |
| 506 | 18 |
| 508 | 6 |
| 500 | 0 |
| 502 | 5 |
| Step 116 Extract | 9 |
| Recrystallized 116 A Extract | 33 |

The strain of *E. coli* used for the tests on adherence to human bladder cells was isolated from an active bladder infection in a human subject. This strain, designated the #3B strain, appears to possess both type 1 and P-type pili.

Results of the agglutination test for various substances and for the two *E. coli* strains are shown in TABLE VI. "Gp" indicates guinea pig cell assay, while "HU" indicates human cell assay. In the guinea pig assay, the highest concentration of final extract (step 116 of FIG. 1) in a 25 µl test dot was 0.056 mg/25 µl; the highest amount of anthocyanins in a dot was 0.063 mg/25 µl; the highest amount of mannose was 0.10 mg/25 µl. Results of a similar test performed on a sample of the acidified alcohol (step 102) extract, with the maximum amount being 0.4 mg/25 µl dot, are also shown. The anthocyanins used in the experiment shown in Table VI were obtained from cranberries by the procedure of FIG. 10. In Step 1008B, the elution of the cation column with 1% HCl, after collection of the void volume and aqueous washes (step 1008A), was found to selectively recover much or all of the anthocyanin content of cranberry. The anthocyanin preparation did not contain significant amounts of other substances.

TABLE VI

Comparison of Adhesion Inhibition by Extract to that by Known Substances

| Sample ID | Blood | Activity Index |
|---|---|---|
| 1% mannose | Gp | 24 |
| Fraction (116) | Gp | 10 |
| EXPT. 1 | Hu | 13 |
| Fraction (116) | Gp | 9 |
| EXPT. 2 | Hu | 11 |
| Alcohol Extract | Gp | 10 |
| Anthocyanins | Hu | 0 |
| Anthocyanins | Gp | 0 |

From the results in Tables V and VI, it is apparent that the cranberry extract inhibits both type 1 pili-mediated adhesion of *E. coli* to guinea pig RBC and adhesion mediated by P-type pili. Since the extract contains virtually no free monomer or dimer sugars, the inhibition of either type of adhesion cannot be attributed to such sugars. Interestingly, P-type adhesion is believed to occur at high levels in *E. coli* in urinary tract infections:

The extract also reduced the adherence of *P. aeruginosa* to bladder epithelial cells, although to a lesser degree than observed with *E. coli*. There was no apparent effect upon the adherence of several Lactobacillus strains to human bladder cells.

Additionally, *E. coli* did not adhere to polystyrene plastic in the presence of the extract. However, it should be noted that, in general, *E. coli* do not tend greatly to adhere to polystyrene.

Example #3

Comparison of extract yields using different metal compounds in Step 104:

Four hundred twenty (420) grams of cranberries were ground with 420 ml of acidified alcohol, and the mixture was allowed to stand overnight. The mixture was centrifuged, the supernatant #1 separated and set aside, and the solid pellet #1 ground with an additional 1200 ml of acidified alcohol. The ground pellet #1 mixture was centrifuged, the supernatant #2 set aside, and the pellet #2, in turn, ground with 1000 ml of acidified alcohol (HCl/MeOH). The ground pellet mixture #2 was again centrifuged and the supernatant #3 was combined with supernatants #1 and #2.

The combined supernatants were evaporated to a volume of 450 ml having a pH of about 1.7. The mixture was divided into six portions of about 75 ml each. To each of the 75 ml portions, 20 ml of 15M $N_4OH$ was added, bringing the solution to a pH of about 8.5 to 8.8. Individual samples were then respectively mixed with 100 ml of a 1.1M solution of each of the following: zinc acetate, zinc sulfate, calcium acetate, barium acetate, cupric acetate, and cobalt acetate. The samples were centrifuged, the supernatant discarded, and each pellet washed three times with 100 ml of 80% EtOH in water each time. The wash supernatants were discarded.

Next, to each pellet, 20 ml of n-butanol and an amount of concentrated HCl (aq) sufficient to reduce the pH to less than about pH 2.5 were added (step 108), generally about 0.75 ml of HCl with certain exceptions as noted in Table VII. The zinc sulfate-treated sample produced a relatively large pellet to which it was necessary to add an additional 0.8 ml of HCl to achieve satisfactory solubilization of the pellet. For the barium acetate sample, an additional 0.25 ml of HCl was needed to react the pellet. The pH of all the samples ranged between about 0.8 and 2.5.

The six samples were again centrifuged and the pellets discarded. The butanol supernatant of each of the six samples was subjected to petroleum ether extraction (step 110), with a sufficient number of back-extractions with water to transfer essentially all the red color from the organic phase to the aqueous phase. Results of the petroleum ether extraction for the six samples (step 110) are summarized in Table VII.

The aqueous layer of each sample was then extracted 3 times with 50 ml EtAc (Step 114). The zinc acetate-treated sample yielded about 150 ml of orange-red ethyl acetate phase. The zinc sulfate sample yielded about 150 ml of dark red solution. The calcium acetate sample produced about 150 ml of a yellow-orange solution. The barium acetate-treated sample produced about 150 ml of a light yellow solution, while the cupric acetate sample yielded about 150 ml of an intense yellow solution, and the cobalt-treated sample resulted in about 150 ml of a yellow solution.

The separated EtAc phase of each of the samples was evaporated to dryness (except for the zinc sulfate sample, which did not become fully dry), producing a red powdery residue. The recovered weight of the dry extracts was as follows: zinc acetate, 63 mg; zinc sulfate, 2980 mg; calcium acetate, 31 mg; barium acetate, 113 mg; cupric acetate, 14 mg; and cobalt acetate, 26 mg.

Example #4

A second comparison of yield using different metal compounds in Step 104 was performed in the same manner as for EXAMPLE #3. The results are included in Table VII. The dry weight yields were: zinc acetate, 46 mg; nickel acetate, 14 mg; magnesium acetate, 17 mg; sodium acetate, 18 mg; and ammonium acetate, 1 mg.

TABLE VII

| Sample | Vol. Petr. Ether | No. Back-Extr. | Aqu. End Vol. |
| --- | --- | --- | --- |
| EXAMPLE #3 | | | |
| Zinc acetate | 100 ml | 2 | 30 ml |
| Zinc sulfate | 300 ml | 1 | 25 ml |
| Calcium acetate | 100 ml | 2 | 30 ml |
| Barium acetate | 300 ml | 3 | 50 ml |
| Cupric acetate | 100 ml | 2 | 30 ml |
| Cobalt acetate | 100 ml | 2 | 30 ml |
| EXAMPLE #4 | | | |
| Zinc acetate | 100 ml | 3 | 40 ml |
| Nickel acetate | 100 ml | 3 | 30 ml |
| Magnesium acetate | 100 ml | 3 | 30 ml |
| Sodium acetate | 100 ml | 3 | 25 ml |
| Ammonium acetate | 100 ml | 3 | 20 ml |

Example #5

Figure 8:
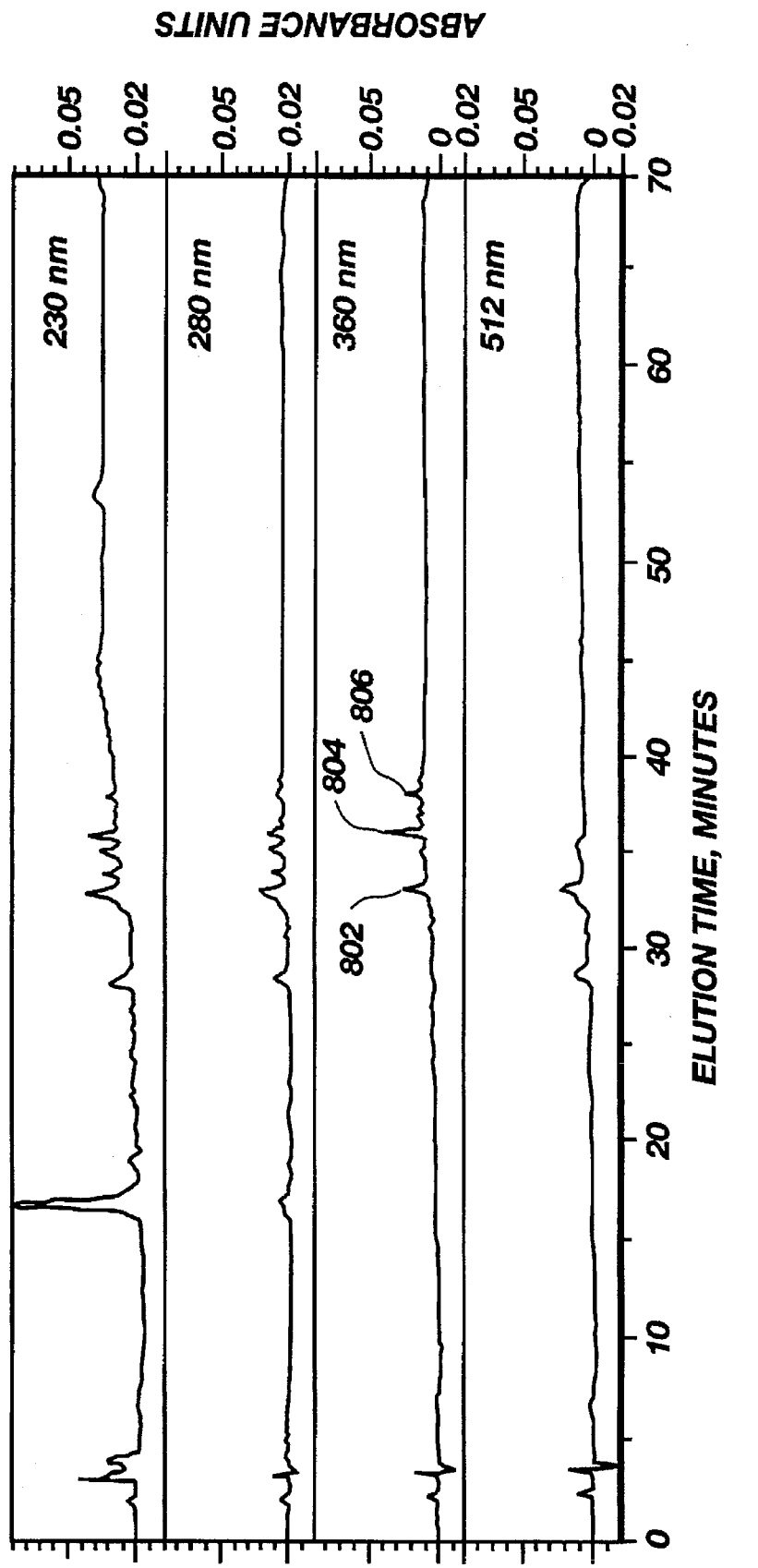
FIG. 8 depicts a chromatogram of a first-step extract of crushed cranberries analyzed at multiple wavelengths.

FIG. 8 shows a chromatogram of the initial liquid extract resulting from step 102, made from cranberries. The liquid extract (the aqueous supernatant after removal of the alcohol) had a volume approximately the same as the starting volume of cranberries (see Example #3). This chromatogram differs from that of FIGS. 5A, 5B, 6A, and 6B in that a different column size, with 4 µm particle size packing, was used with a slightly different procedure. To obtain this chromatogram, an analytical C18 column of dimensions 8 mm diameter, 100 mm length and a volume of 5 ml was used. The concentration by mass of material in the extract was about 200 mg per ml (determined from an aliquot of the liquid extract evaporated to dryness). Fifty µl of a 200 mg/ml solution (total mass 10 mg) was injected into the column and a flow rate of 1 ml/min was used. Under these conditions, the most prominent elution peaks 802, 804, 806 absorbing at 360 nanometers have retention times of about 33, 36, and 38 min., respectively.

Example #6

FIG. 9 depicts a chromatogram of the cranberry extract resulting from step 116, eluted by the alternate protocol on a preparative-size (50 ml) C18 column. In this case, 50 µl of a 50 mg per ml solution of the cranberry extract was injected onto the column (2.5 mg total mass). Three prominent 360 nm-absorbing peaks 902, 904, 906 are also seen in the chromatogram of FIG. 9, having retention times of about 34, 39, and 43 min. It will be seen that the retention times of the 360 nm-absorbing peaks differ somewhat from those of the chromatograms of FIGS. 5 and 6, which were obtained on preparative-size columns of 25 mm diameter, 100 mm length, volume 50 ml, also with C18 type particles. These peaks are slightly shifted from those of FIG. 8, by an amount consistent with the 5-min. difference in timing of the gradient between the analytical column of FIG. 8 and the alternate (shortened) preparative column protocol.

The following computation provides a rough estimate of the relative enrichment for 360 nm-absorbing compounds (flavonoids) in the final cranberry extract. The area under the peaks absorbing at 360 nm in FIG. 9 is about 2.6 A.U. (absorbance units), while that for the 360 nm-absorbing peaks in FIG. 8 is about 0.12 A.U. Dividing 2.6 by 0.12, and multiplying the result by 4, the factor of the difference in mass applied to the column (4 times as much material loaded for FIG. 8 as for FIG. 9), the enrichment for 360 nm-absorbing compounds in the cranberry extract of step 116 over the levels in the initial liquid extract is seen to be about 87-fold. From the rough computation and similar rough estimates made from other samples, it appears that the degree of enrichment for 360 nm-absorbing compounds (which are presently believed to be polyphenols) is similar to the degree of enrichment for anti-adherence activity in the final cranberry extract.

Example #7

Figure 11A:
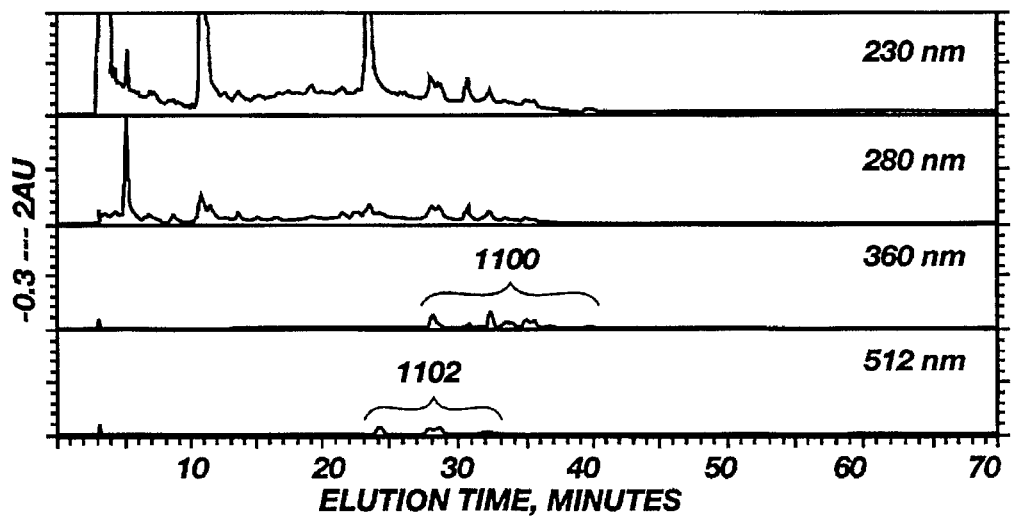
FIGS. 11A–11F are HPLC chromatograms of products of selected steps in the process of the invention.
Figure 11B:
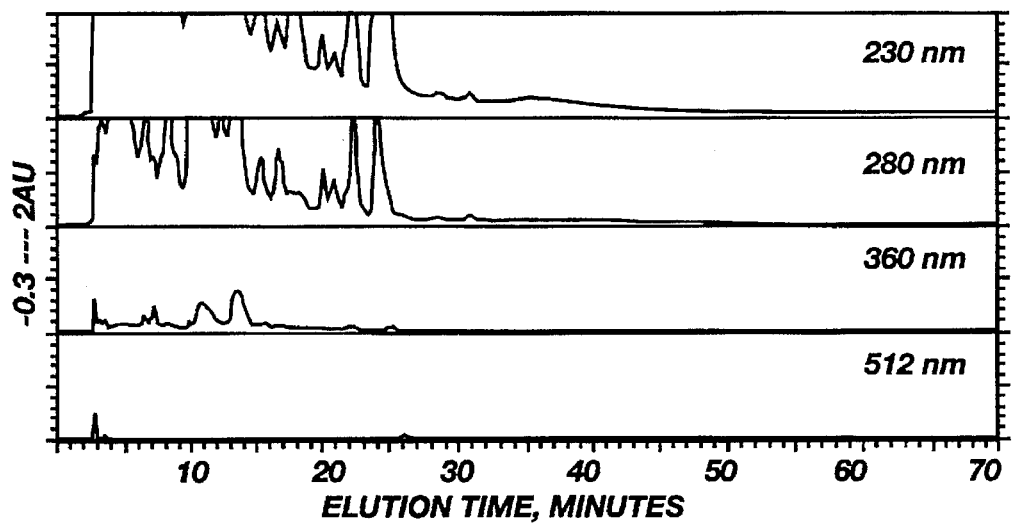
Figure 11C:
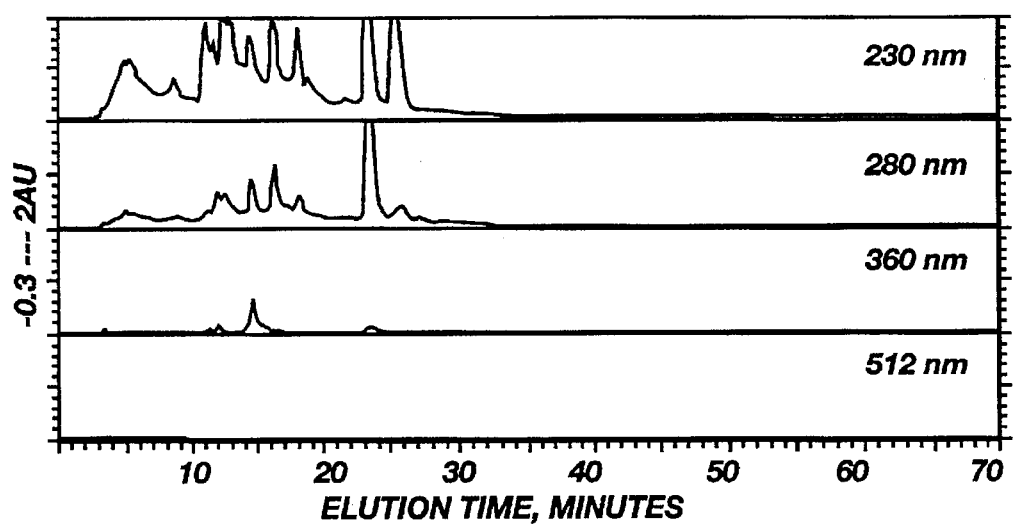
Figure 11D:
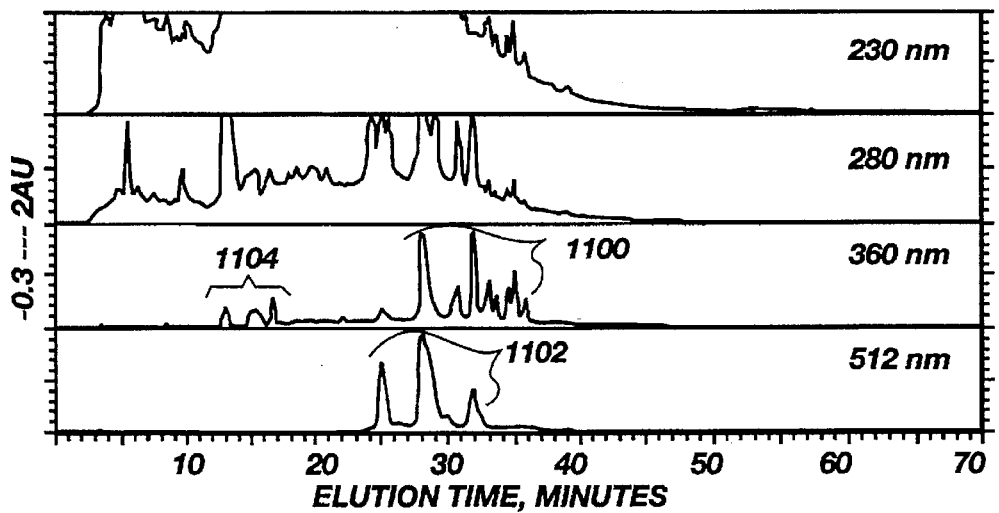

FIGS. 11A–F are chromatograms on a C18 column of selected preparations, including some from Table VIII. FIG. 11A is a chromatogram of sample #18 in Table VIII, which is a 10% solution of OCEAN SPRAY™ cranberry powder. FIGS. 11B and 11C are chromatograms of the water washes of the C18 column from step 1000, corresponding to samples #19, #20 in Table VIII. FIG. 11D is a chromatogram of the MeOH eluate from step 1000 (FIG. 10) containing the active fraction and corresponding to sample #21 in Table VIII. In FIG. 11D a group of 360 nm-absorbing peaks 1100 eluting at between 30 and 42 minutes can be seen. This group of peaks is not detectable in FIG. 11B or 11C, and the relative amount of material eluting in these peaks is much less in the starting material (FIG. 11A). A group of elution peaks 1102 absorbing at 512 nm, characteristic of anthocyanins, is also seen in FIG. 11D.

Figure 11E:
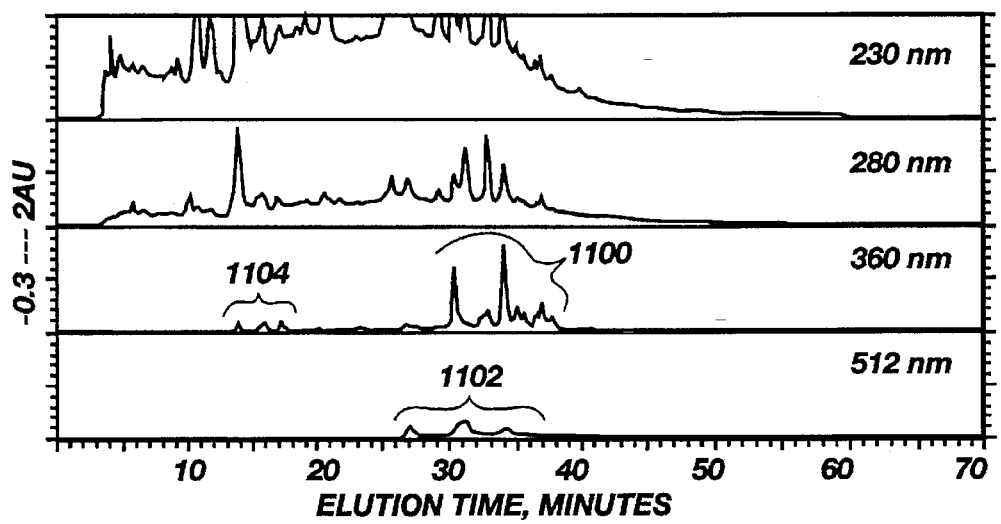
Figure 11F:
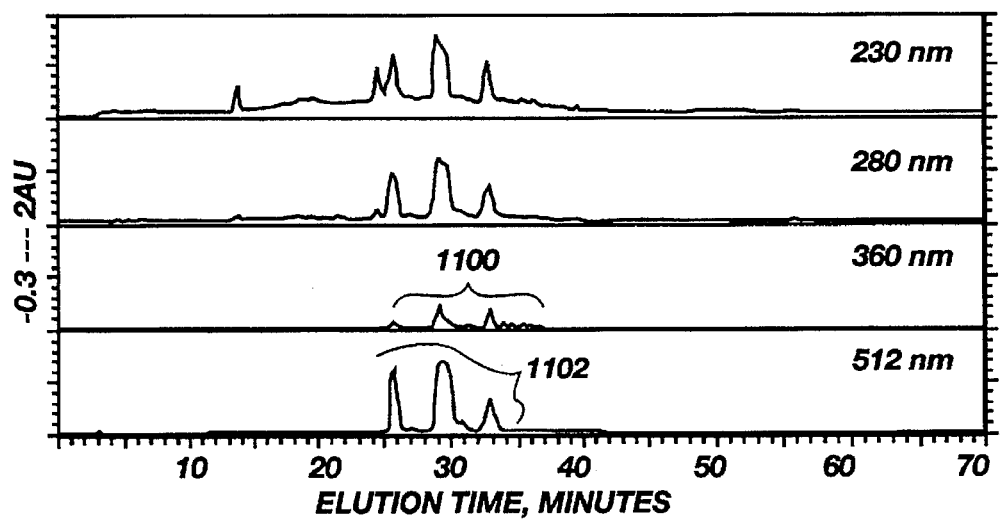

FIG. 11E is a chromatogram of a sample which has been further subjected to cation chromatography, step 1008, corresponding to sample #23 of Table VIII. Peaks 1100 are still present in an amount similar to that of FIG. 11D, but peaks 1102 (the anthocyanins) are considerably reduced in amount. Additionally, a group of small peaks 1104 eluting at about 23 to about 27 min. I detectable. FIG. 11F is a chromatogram of an HCl eluate of the cation column, corresponding to sample #24. Peaks 1102 are present in substantial amount, while peaks 1100 are nearly absent.

TABLE VIII

Anti-Adhesion Activity of Selected Products During Preparation of Extract

| Sample | Normalized activity[1] |
| --- | --- |
| 1. MAW initial extract | 14.9 |
| 2. ---ppt. from initial extract | 1.2 |
| 3. Prior to EtAc extraction (step 110, FIG. 1) | 5.7 |
| 4. Step 114, aqueous phase | 8.4 (16.8, 0.0) |
| 5. Step 116 (evap. organic phase) | 33.8 (117.7, 0.0) |
| 6. EtAcEt[2] 10:1:5 initial extract | 4.3 |
| 7. ---ppt. from initial extract | 3.9 |
| 8. EtAcEt 5: 1: I 0 initial extract | 0.0 |
| 9. ---ppt. from initial extract | 7.7 |
| 10. EtAc initial extract | 3.3 |
| 11. ---ppt. from initial extract | 6.4 |
| 12. Boiling water | 6.1 |
| 13. ---ppt. from initial extract | 5.3 |
| 14. ---Step 1002 product | 23.9 |
| 15. Refluxed water | 4.1 |
| 16. ---ppt. from initial extract | 6.6 |
| 17. ---Step 1002 product | 39.4 |
| 18. 10% OCEAN SPRAY ™ powder | 4.6 |
| 19. Step 1001 wash discard | 4.1 |
| 20. Step 1001, 2nd wash discard | 0.0 |
| 21. Step 1002 product | 34.5 |
| 22. CHCl₃/EtAc extract of 1002 prod. | 22.7 |

TABLE VIII-continued

Anti-Adhesion Activity of Selected Products During Preparation of Extract

| Sample | Normalized activity[1] |
| --- | --- |
| 23. Step 1008A product | 45.1 |
| 24. Step 1008B HCl eluate | 0.0 |
| 25. Step 1008C methanol eluate | 92.1 |

[1] 1% mannose in water = 100
[2] EtAcEt = ethyl acetate/acetic acid/ethanol

Comparison of the RBC assay values and the chromatograms for the samples of FIGS. 11A–11F reveals that the presence of significant activity in the RBC assay is positively correlated with the presence of peaks 1100.

Example #8

Figure 12:
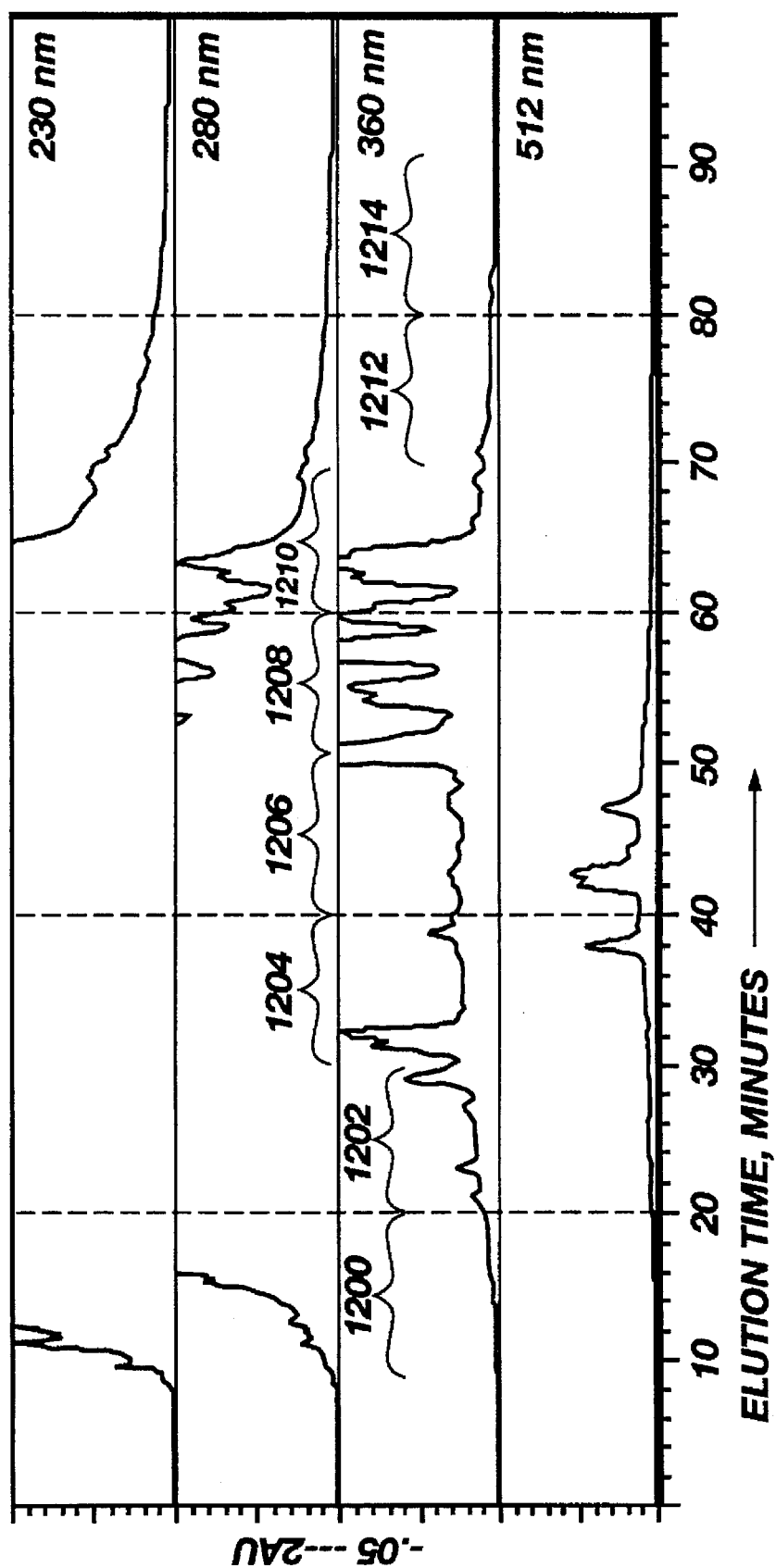
FIG. 12 is a chromatogram of a product of FIG. 10 indicating collection of sequential fractions for activity analysis.

A sample of the product of step 1006 in the process of FIG. 10 was subjected to HPLC on a 50 ml C18 column (FIG. 12). The indicated fractions 1200, 1202, 1204, 1206, 1208, 1210, 1212, 1214 were collected and analyzed in the RBC assay (Table IX) at the various elution times depicted on the x-axis in minutes. Since fractions 1200–1208 all contained significant levels of activity, it appears that the extract contains multiple components contributing to the anti-adhesion activity. From the data, it also appears that polyphenols contribute anti-adhesion activity to the extract. Polyphenols absorb UV wavelengths strongly (at 230 nm and 280 nm). Fractions 1200, 1202 and 1204, which have little material absorbing at 360 nm, have significant elution peaks of material absorbing at 230 and 280 nm, in the wavelength range expected for polyphenols. It is known that polyphenols may be retained on lipophilic columns similar to the C18. Thus, one might expect an extract produced by the process to include polyphenols.

TABLE IX

Comparison of Activity in Selected HPLC Fractions

| Sample | Normalized Activity* |
| --- | --- |
| 1200 | 10.5 |
| 1202 | 25.1 |
| 1204 | 37.8 |
| 1206 | 45.1 |
| 1208 | 41.6 |
| 1210 | 0.0 |
| 1212 | 0.0 |
| 1214 | 0.0 |

*1% mannose in water = 100

Example #9

Figure 14A:
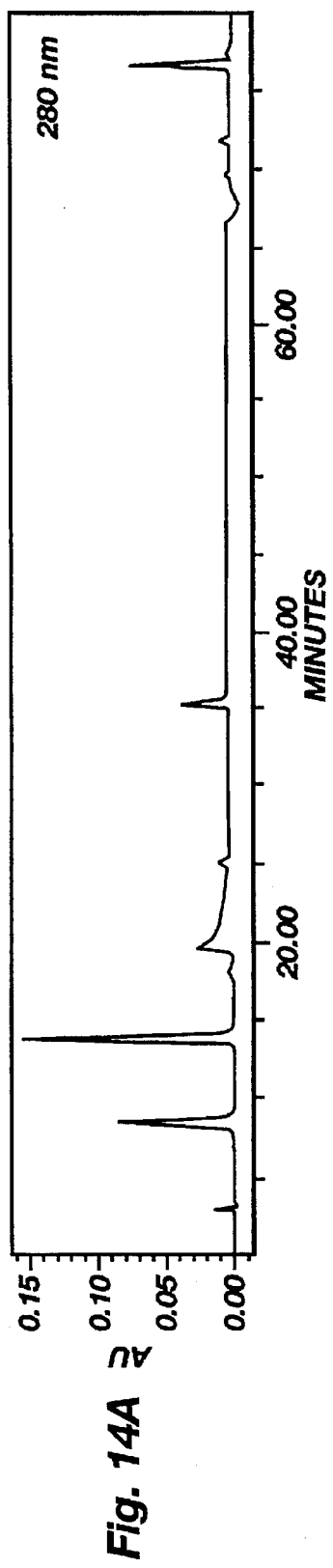
FIGS. 14A–14G depict HPLC chromatograms of the products from selected steps of the process outlined in FIG. 13.
Figure 14B:
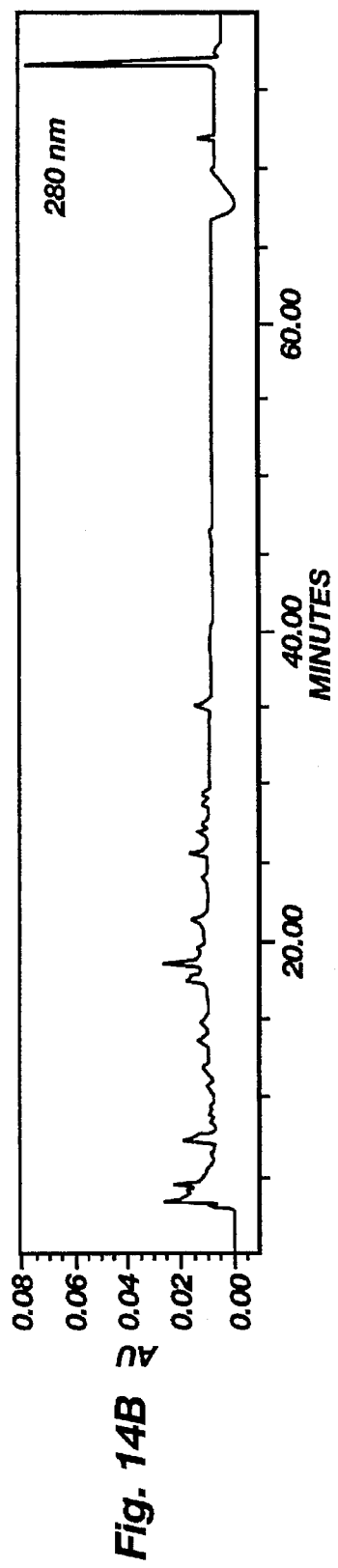
Figure 14C:
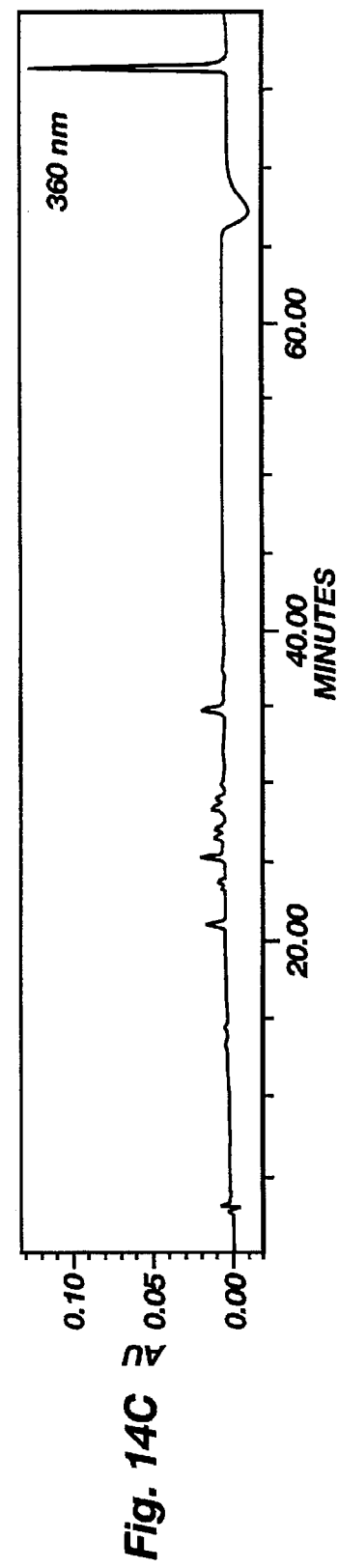
Figure 14D:
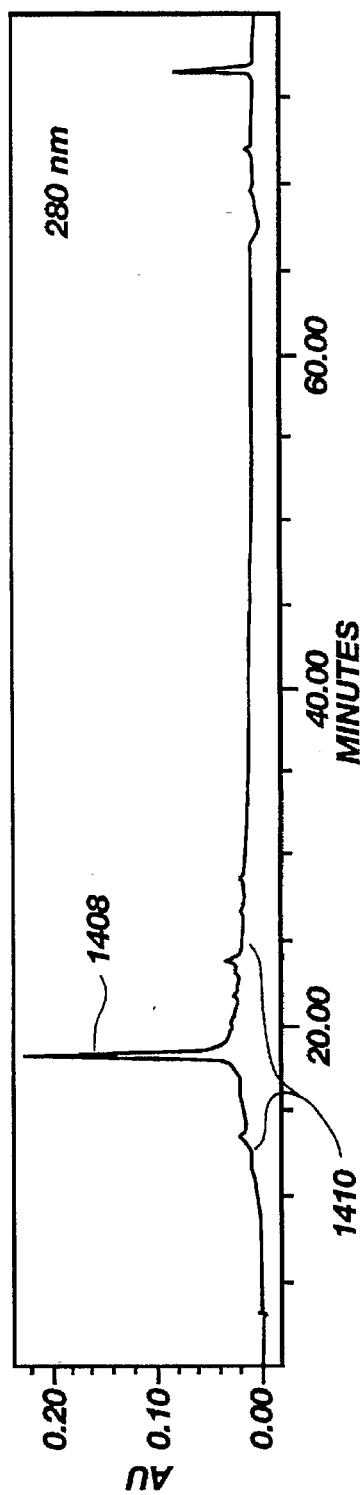
Figure 14E:
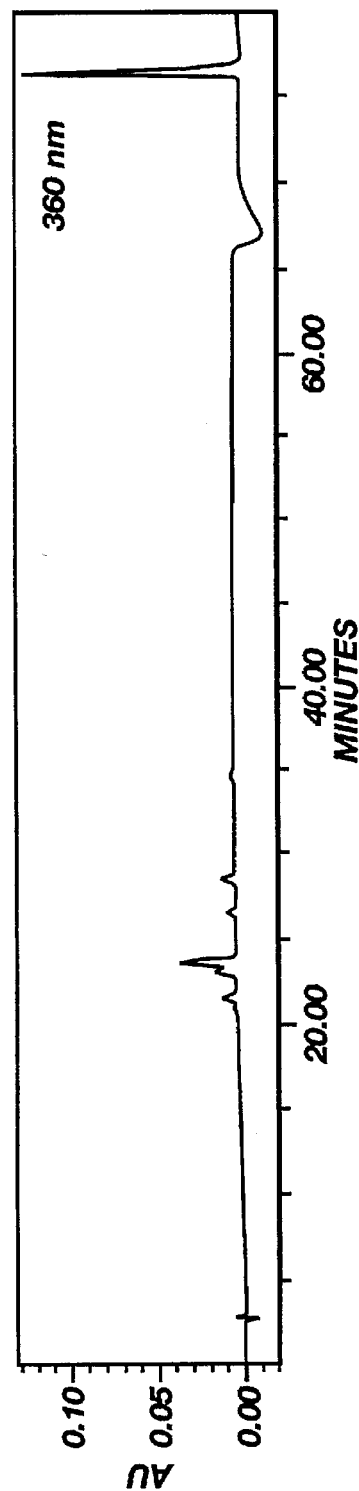
Figure 14F:
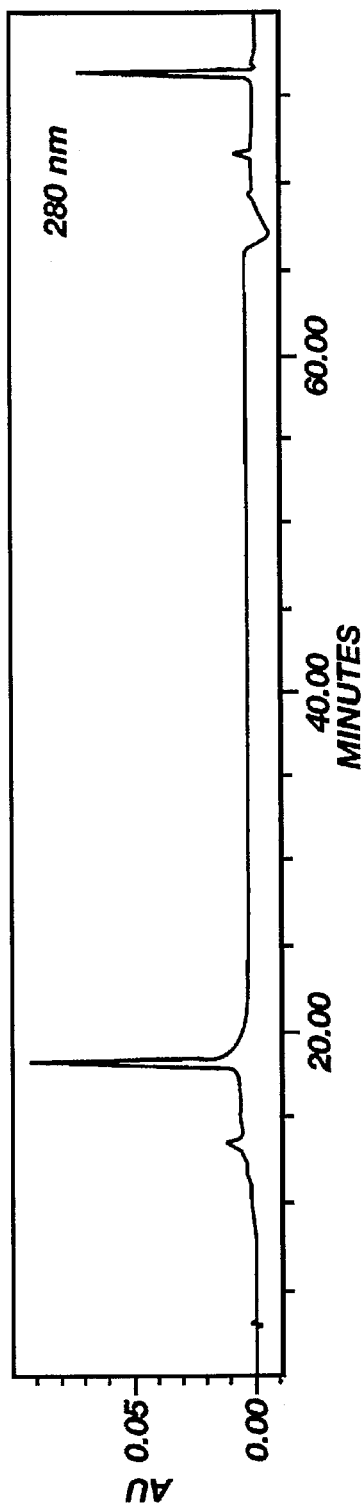
Figure 14G:
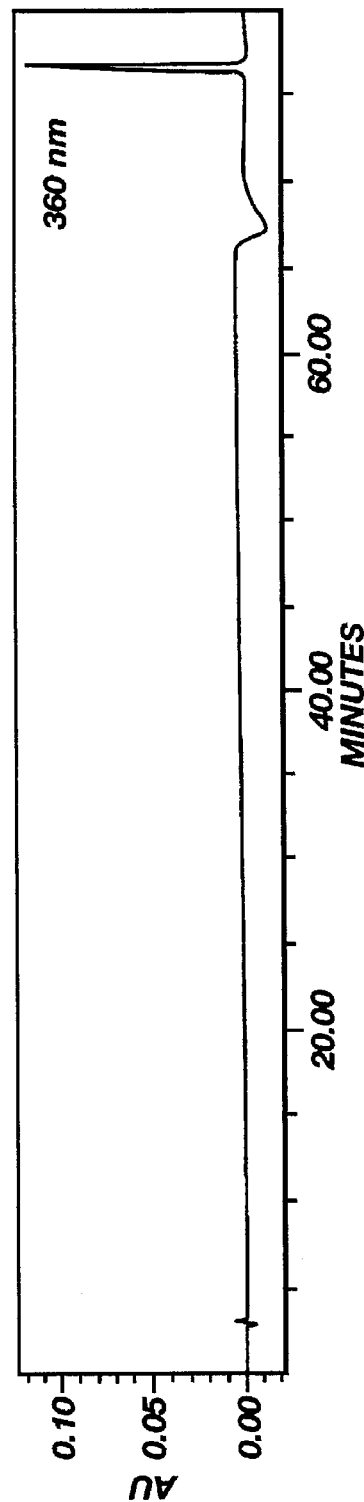

FIGS. 14B–14G depict analytical HPLC chromatograms of products from various steps of the process of FIG. 13. FIG. 14A is an HPLC chromatogram showing the retention time of two marker standards, catechin (peak 1400) and epicatechin (peak 1402), in the same HPLC protocol as FIGS. 14B–G. FIGS. 14B & 14C are chromatogram of the product of step 1304, analyzed for compounds absorbing at 280 nm and for compounds absorbing at 360 nm. FIGS. 14D & 14E show chromatograms of the product of step 1316, also analyzed for compounds absorbing at 280 nm and at 360 nm. FIGS. 14F & 14G show chromatograms of the product of step 1316A, from which it is evident that essentially no 360 nm-absorbing compounds remain.

The eluate of step 1316A has been subjected to $^{13}C$ and $^{1}H$ nuclear magnetic resonance (NMR) analysis, mass spectrometry, and infrared absorbance analysis.

Figure 15:
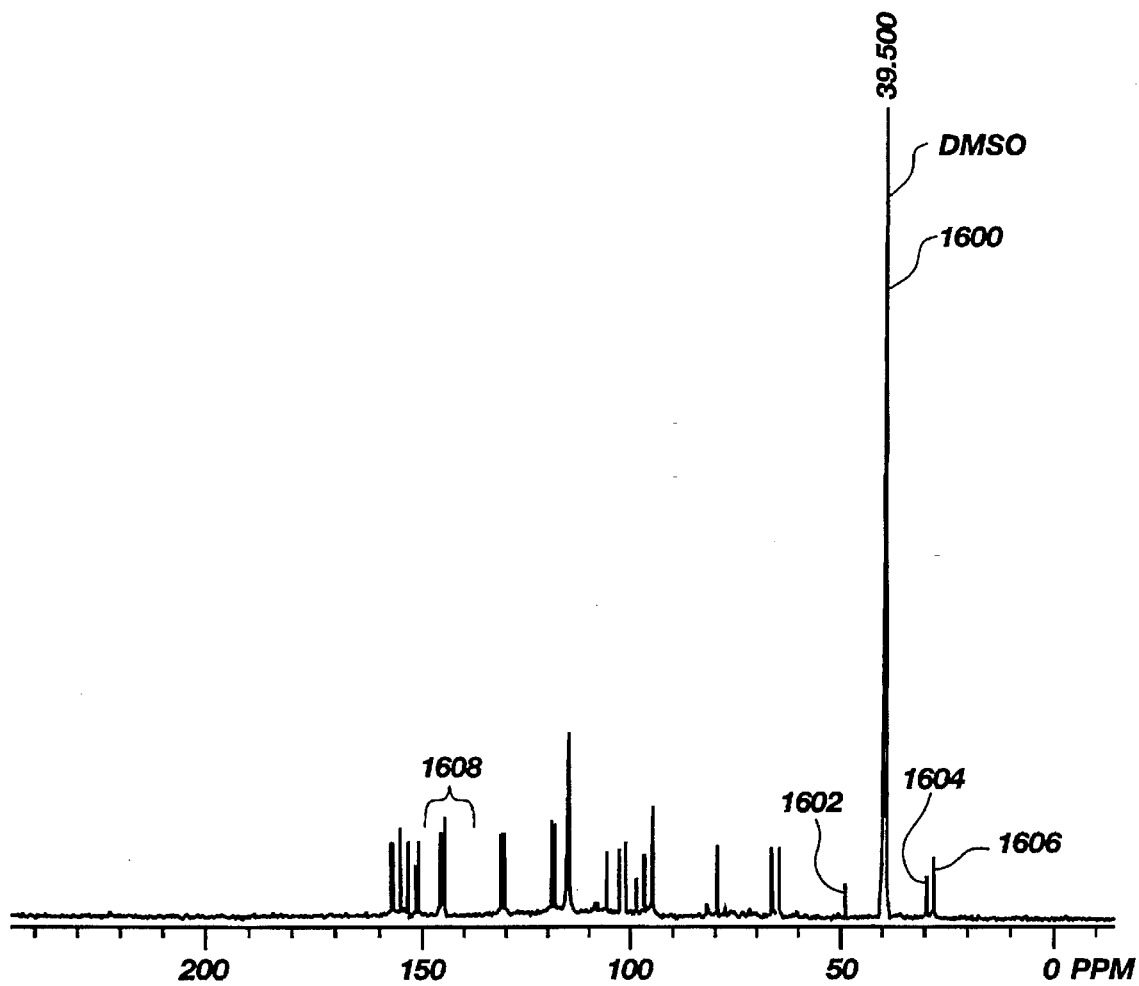
FIG. 15 is a chart depicting a $^{13}C$ NMR spectrum of the isolated active material isolated as per FIG. 13.

FIG. 15 depicts a $^{13}C$-NMR scan of product from step 1316A, in $d_6$-dimethyl sulfoxide (DMSO). Peaks 1600 and 1602 are from the DMSO and MeOH solvents, respectively. Peak 1604 represents a C4 carbon of an epicatechin ring system, while peak 1606 represents a C4 carbon of a catechin ring system. Peaks 1608 represent the C3 and C4 carbons of a B-ring of a flavonol (catechin) ring system. The following information may be useful in interpreting the NMR of FIG. 15:

Pulse Width=12.00 μSEC
ACQ Time=60 DEGREES
Recycle Time=819.20 MSEC
No. of ACQS=0.99 SEC
Decoupler: Standard-64 Modulation
Frequency=4.000 PFM
Power=2900/3000

Figure 16:
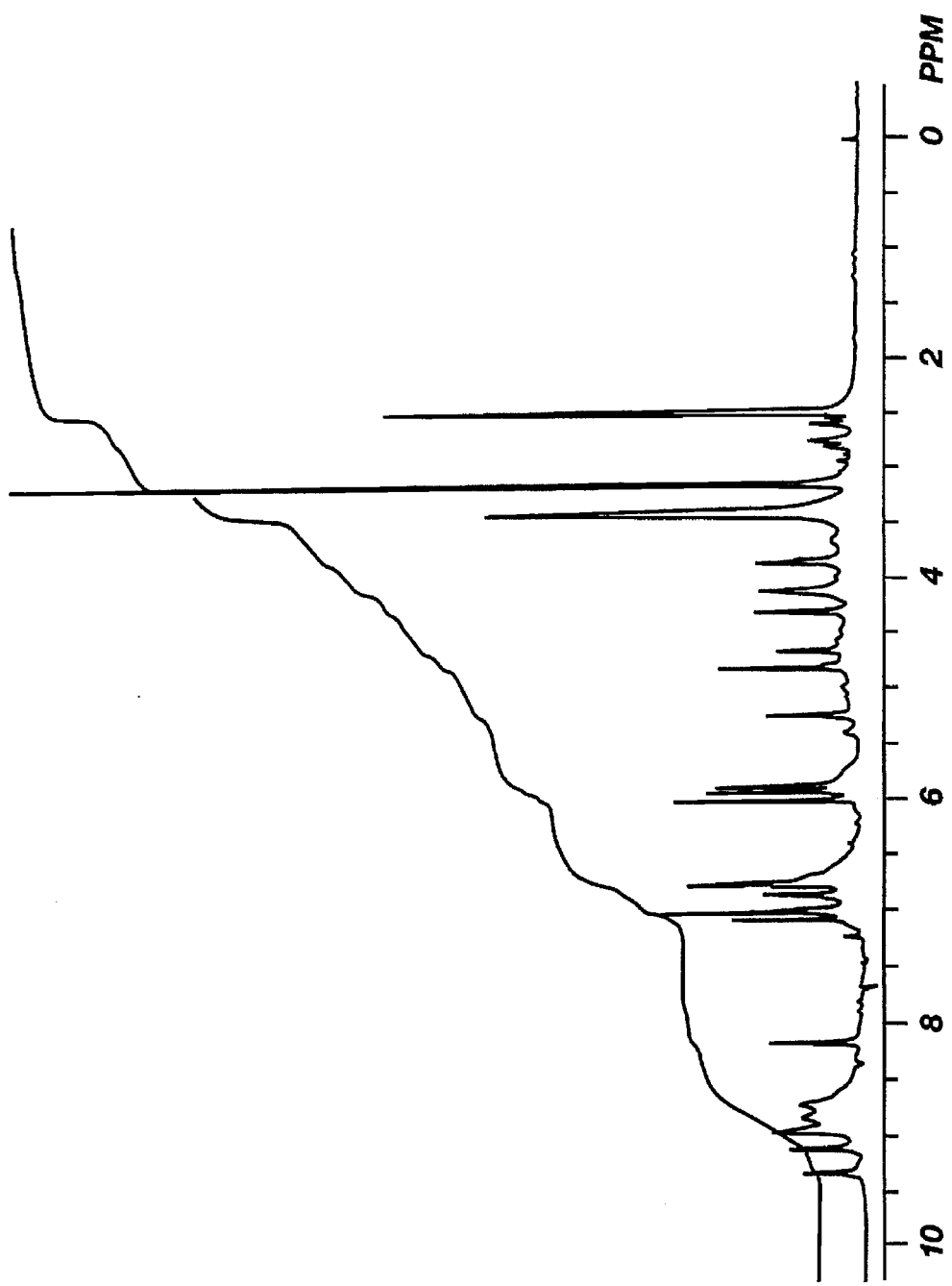
FIG. 16 is a chart depicting a $^{1}H$ NMR spectrum of the isolated active material isolated as per FIG. 13.

FIG. 16 depicts an $^{1}H$-NMR scan of product from step 1316A, also in $d_6$-DMSO. The following information may be useful in interpreting the NMR of FIG. 16:

| One Pulse Sequence |
| --- |
| Pulse Width = 3.00 μSEC |
| = 30 DEGREES |
| ACQ Time = 1.36 SEC |
| Recycle Time = 3.74 SEC |
| No. of ACQS = 64 |

Figure 17A:
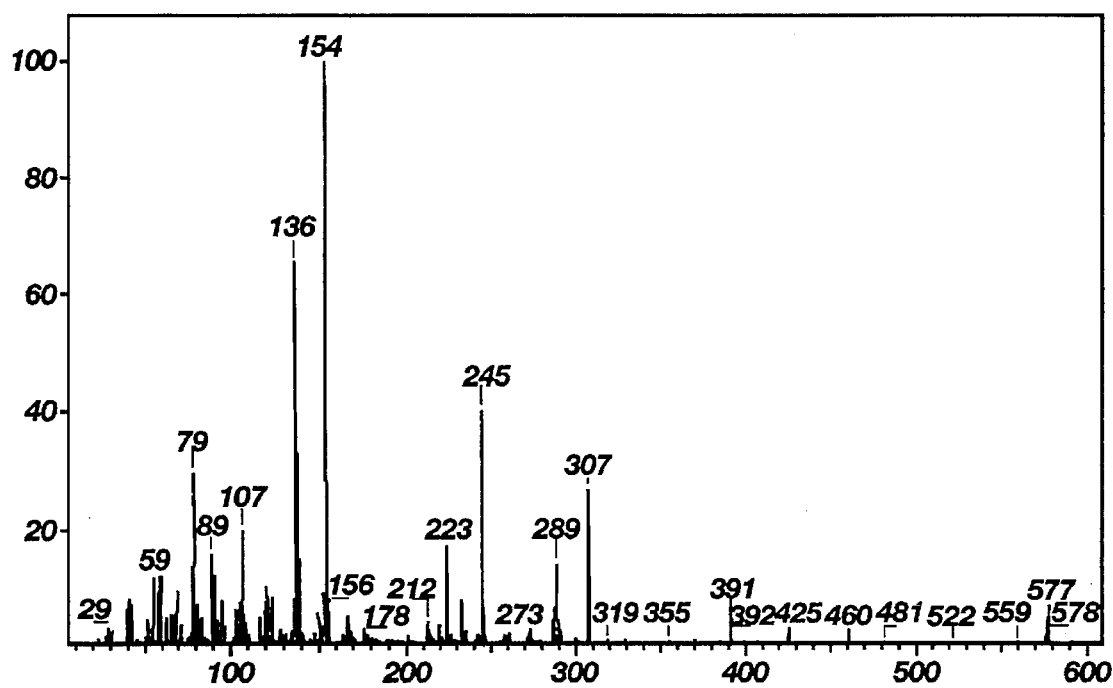
FIG. 17A & 17B are charts of mass spectrograms of isolated active material isolated as per FIG. 13.
Figure 17B:
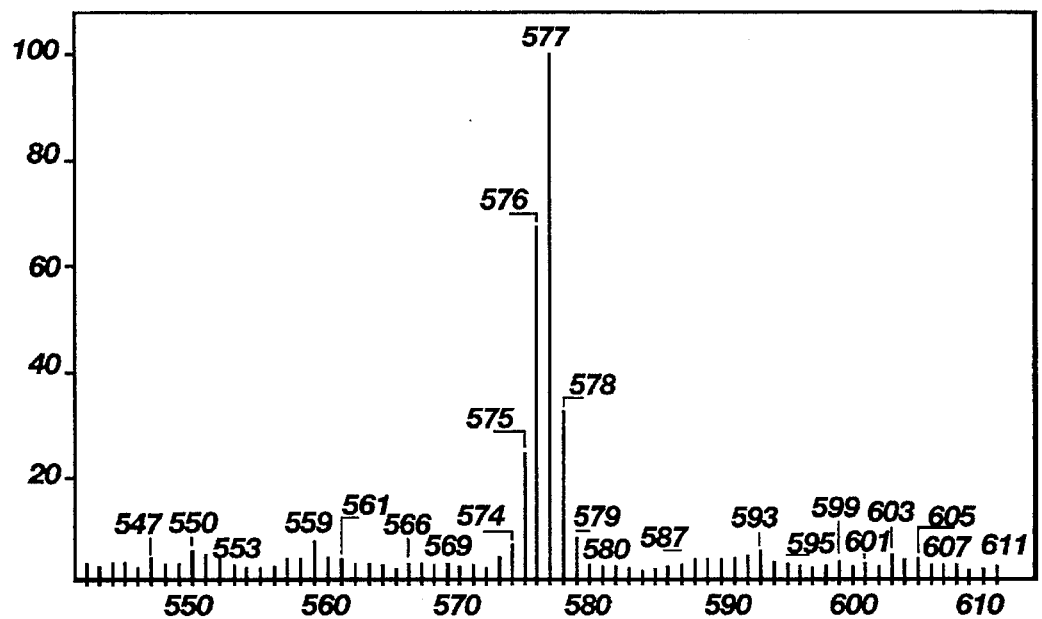

FIGS. 17A & 17B depict a mass spectrogram of product from step 1316A, dissolved in 3-nitrobenzyl alcohol with DMSO.

Proanthocyanidin oligomers or polymers, useful for the present anti-microbial methods are comprised of monomeric units of leucoanthocyanidins. Leucoanthocyanidins are generally monomeric flavonoids which include catechins, epicatechins, gallocatechins, galloepicatechins, flavanols, flavonols, and flavan-3,4-diols leucocyanidins and anthocyanidins. The proanthocyanidin polymers have 2 to 30 flavonoid units, preferably 2 to 15 flavonoid units, and most preferably 2 to 11 flavonoid units.

Proanthocyanidin polymers having a varying number of flavonoid units are known and have been reported, for example, in W. L. Mattice, et al., *Phytochemistry*, 23, p. 1309–1311 (1984); Z. Czochanska, et al., *J. C. S. Chem. Comm.*, 375 (1979); W. T. Jones, et al., *Photochemistry*, 15, p. 1407–1409 (1976); E. Haslam, *Plant Polyphenols*, p. 75 (1989), which are all incorporated by reference. Those polymers having the recited ranges of flavonoid units and described in these references are useful for the methods of the present invention.

Additionally, the crystalline compound is found to have a melting point (M.P.) of greater than 280° C., and is observed to be extremely stable to oxidation during storage in atmosphere; leucocyanidins are known to have such a property.

From the above data, it is evident that the product from step 1316A has many of the characteristics of a procyanidin. In addition, it is further believed that in addition to the dimer, the material in the region 1410 beneath the peak 1408 of the HPLC of FIGS. 14D & 14E comprises polymeric procyanidins of various chain lengths up to 5000 Daltons molecular weight and that these are highly active as well.

In addition, it was found that crystal formation (1316A) occurred upon storage of the LH-20 70/30 eluate under nitrogen for periods of from one to several weeks or more (FIG. 13). Apparently, under slow purging of the nitrogen atmosphere, the eluate (generally 1–2 ml volume) becomes sufficiently concentrated that the purified active compound spontaneously crystallizes; such behavior is known for various polyphenolic compounds. Needle-like crystals are obtained from water, alcohol (e.g. MeOH or EtOH) or mixtures thereof.

Certain other compounds present in the extract have been further identified as having anti-adhesion activity, and in some cases are partially purified. These include leucocyanidins/leucodelphinidins and flavonol pyranosides. Catechin is described in the Merck Index #1908; epicatechin differs from catechin in the orientation of the hydroxyl at position 3, and the hydrogen at position 2 of ring C of Compound IV. Procyanidins, also referred to as proanthocyanidins, are polymeric compounds composed of catechin and epicatechin residues; substance I depicts a dimer of epicatechin and catechin, with the epicatechin linked via C4 to the C8' of the catechin moiety. A repeating unit of a polymeric procyanidin; catechin and epicatechin residues may be combined in all possible combinations in polymeric procyanidins up to molecular weights of up to about 5000 Daltons. Proanthocyanadin polymers are known to have a varying number of flavonoid units. The polymers preferably contain two to fifteen monomeric flavonoid subunits, most preferably two to eleven subunits. Leucocyanidin is described as Merck Index #5334; a closely-related compound is leucodelphinin. Myricetin-3-pyranoside, a compound identified and described as isolated from the present extract and found to have activity; myricetin is Merck Index #6244.

The anti-adhesion activity of the putative procyanidin and procyanidin polymers is believed to be potentiated or otherwise enhanced when combined with a substance selected from the group comprising Vaccinium-derived flavanols, especially galloyl-substituted polyphenols including gallocatechin, gallo-epicatechin, and pyranosides or sulfates of these; Vaccinium-derived leucocyanins; and Vaccinium-derived flavonol pyranosides.

Of the flavonol pyranosides present in the Vaccinium extract, myricetin-3-pyranoside exhibits the highest anti-adherence in a metabolically unactivated form. In its native state, this compound has anti-adhesion activity, but less than that of the procyanidin(s).

In general, compounds having a ring system as shown in formula IV, wherein the ring C includes oxygen at position 1 and having a pyranoside as R2 has anti-adhesion activity. The ring C is saturated except for the C=C bond shared with ring A. Evidence for the necessity of the unsaturation of ring C and the necessity of R2 being a pyranoside is as follows. Leucoanthocyanins (exemplified as leucocyanin and leucodelphinin, see FIGS. 14A–14G) are colorless compounds having the catechin or epicatechin ring structure with a saturated ring C and a pyranoside in the R2 position. Upon treatment of leucocyanins by heating in aqueous acid solution, the O-R2 carbohydrate linkage is hydrolyzed oxidized and ring C is oxidized, resulting in an unsaturated cyanidin (or delphinidin), wherein ring C is unsaturated and gives a characteristic red color. The material in certain HPLC peaks of the Vaccinium extract, which absorb at 280 nm and are found to contain anti-adhesion activity, are initially colorless. Upon treatment with heat and aqueous acid, carbohydrate moieties are released, ring C is oxidized, and red color appears in the fraction at the characteristic anthocyanin absorbance wavelength of 512 nm, and the activity in the material is lost. The oxidation state of ring C appears to play an important role in the mechanism of anti-adherence activity.

Further, quercetin and myricetin, which both share a slightly more oxidized catechin or epicatechin-like nucleus than the leucocyanins out have R2=H, have been tested in the anti-adhesion assay and show no activity. However, myricetin-3-pyranoside isolated from Vaccinium species does have anti-adhesion activity. Further as described previously herein, one of the anti-adhesion assays described herein compares the ability of a substance to inhibit binding relative to mannose inhibition of such adhesion, and it is therefore believed that a carbohydrate moiety is involved in conferring anti-adhesion activity, regardless of whether it is added prior to or as a result of metabolic activation.

Based on the above observations, it was concluded that structures as shown in formula IV, wherein Z=C or C=O; R1=H or OH, R2=H, OH, pyranoside, a pyranoside chain, or galloyl; R3=H or OH; R4=catechin, epicatechin, or procyanidin polymer; all possess some degree of inhibitory effect on adherence of microbes to cell surfaces. Further, the microbes whose adherence to cells is interfered with include bacteria, yeast and pig which bind to cell surfaces as a first step in infecting them.

The invention is described with reference to specific embodiments, plant species and parts, buffers and chemical procedures and the like. However, it will be recognized by those skilled in the art that various chemical substitutions can be made without departing from the spirit and scope of the invention. In particular, it is known that polyphenols, including flavonoids and anthocyanins, can be isolated and/or partially purified from plant materials by a number of different methods. It will further be recognized that these alternate methods, and consequent changes in other steps of the method including removal of sugars, of various solvents, and of anthocyanins from a composition comprising partially purified polyphenols, fall within the scope of the present invented Vaccinium extract.

What is claimed is:

1. A method of interfering with non-viral microbial tissue adhesion to a body tissue comprising topically administering a proanthocyanidin having a structure selected from I, II and III

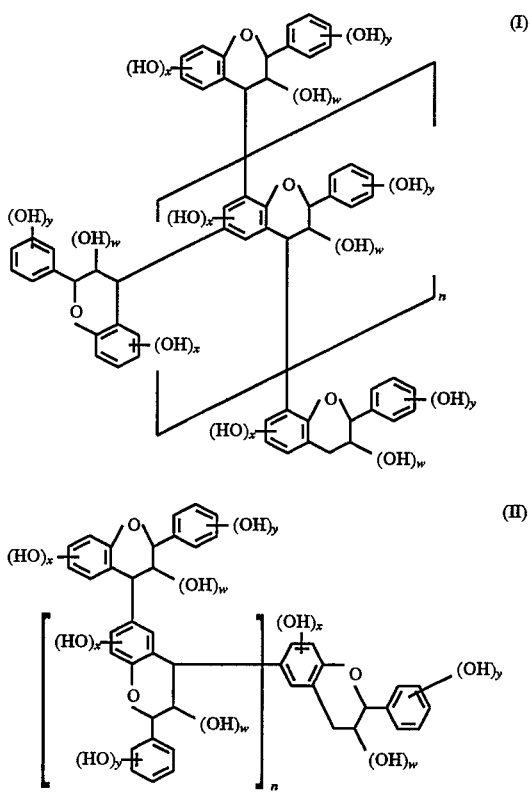

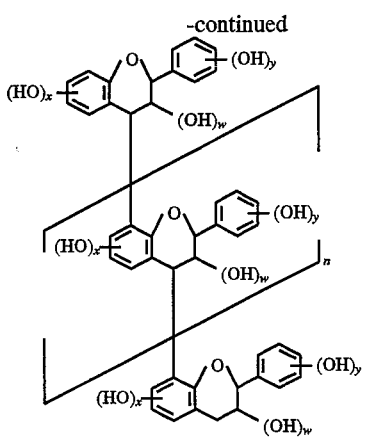

wherein x, y=1 to 3, w=0 or 1, n=0 to 18.

2. The method of claim 1 wherein n=0 to 13.

3. The method of claim 1 wherein n=0 to 9.

4. The method of claim 1 in which the proanthocyanidin monomer or polymer comprises 2 to 30 monomeric flavonoid units having structure IV.

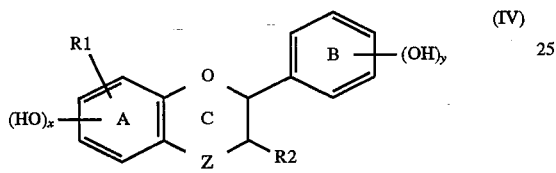

wherein x is 0 to 3; y is 0 to 3; Z is $CH_2$, CHOH, C=O, $CHSO_3H$, galloyl, catechin, or epicatechin; R1 is H, pyranoside, galloyl, catechin, or epicatechin; and R2 is H, OH, pyranoside, or galloyl.

5. The method of claim 4 in which the proanthocyanidin polymer comprises 2 to 15 monomeric flavonoid units.

6. The method of claim 4 in which the proanthocyanidin polymer comprises 2 to 11 monomeric flavonoid units.

7. The method of claim 1, wherein said body tissue is selected from the group consisting of: gums, tooth surfaces, oral cavity mucosal tissues, throat mucosal tissues, genital mucosal tissues, and cervical surface tissues.

8. A method of preparing a plant extract having an active fraction which is active to inhibit adherence of microbes to cell surfaces, comprising:

providing a homogenate of a plant material of a plant having a native active fraction comprising polyphenolic compounds having anti-adherence activity;

adding a sufficient amount of a base to said homogenate to alkalinize said homogenate to a pH of greater than about pH 10 and to cause phenol groups of polyphenolic compounds to be ionized to phenoxide ions; and adding to said alkalinized homogenate, a sufficient amount of an alcohol to produce a precipitate of said polyphenolic compounds having phenoxide ions, and separating said precipitate.

9. The method of claim 8, further comprising:

fractionating said precipitate on a lipophilic column by step-wise elution with solutions containing varying ratios of an organic solvent to water, said organic solvent being water-miscible, beginning with a low organic solvent:water ratio, to produce a series of step-wise eluates eluted at different organic solvent:water ratios; and separating and identifying one of said eluates as substantially comprising said fraction having anti-adherence activity.

10. The method of claim 9, further comprising:

fractionating said anti-adherence eluate on a column to separate substantially colorless polyphenolic compounds from colored anthocyanic compounds;

fractionating the colorless polyphenolic compounds recovered from said column on a second lipophilic column by step-wise elution with solutions containing varying ratios of an organic solvent to water, said organic solvent being water-miscible, beginning with a low organic solvent:water ratio, to produce a second series of step-wise eluates eluted at different organic solvent:water ratios; and separating and identifying one of said second series of eluates as having anti-adherence activity.

11. A method of purifying a proanthocyanidin having a structure selected from I, II and III

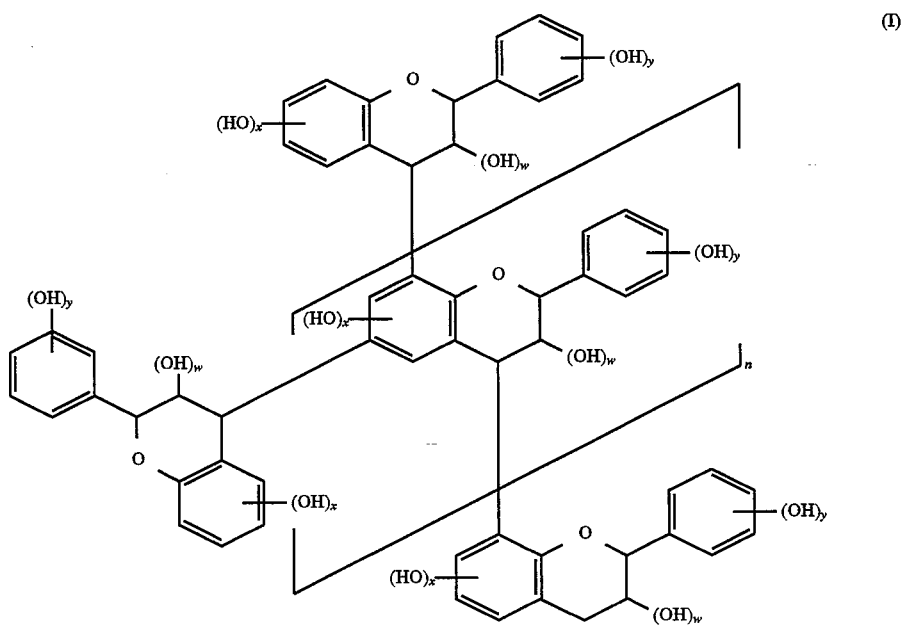

-continued

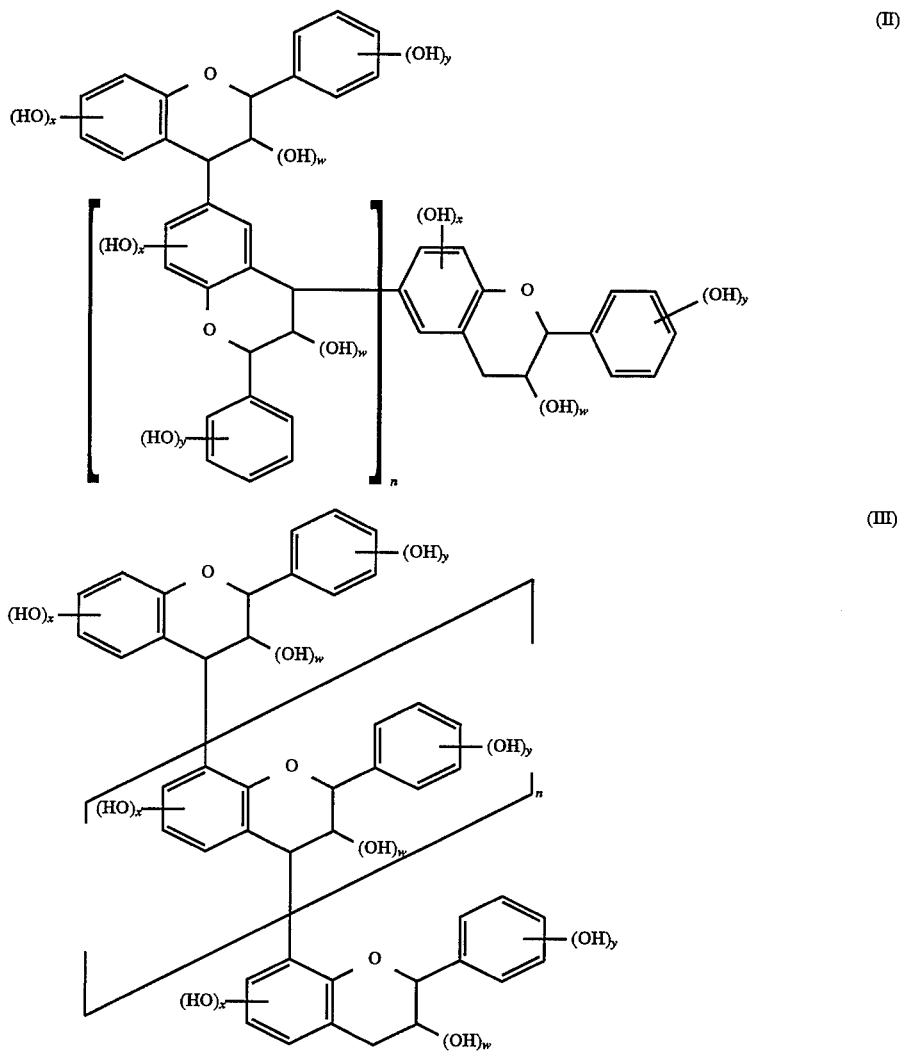

(II)

(III)

wherein x, y=1 to 3, w=0 or 1, n=0 to 18 from plant material, comprising:

providing a homogenate of a plant material of a plant having a native active fraction comprising polyphenolic compounds having anti-adherence activity;

adding a sufficient amount of a base to said homogenate to alkalinize said homogenate to a pH of greater than about pH 10 and to cause phenol groups of polyphenolic compounds to be ionized to phenoxide ions; and adding to said alkalinized homogenate, a sufficient amount of an alcohol to produce a precipitate of said polyphenolic compounds having phenoxide ions, and separating said precipitate.

12. The method of claim 11, further comprising:

fractionating said precipitate on a lipophilic column by step-wise elution with solutions containing varying ratios of alcohol to water, beginning with a low alcohol:water ratio, to produce a series of step-wise eluates eluted at different alcohol:water ratios; and separating and identifying one of said eluates as substantially comprising said fraction having anti-adherence activity.

13. The method of claim 12, further comprising:

fractionating said anti-adherence eluate on a column to separate substantially colorless polyphenolic compounds from colored anthocyanic compounds;

fractionating the colorless polyphenolic compounds recovered from said column on a second lipophilic column by step-wise elution with solutions containing varying ratios of alcohol to water, beginning with a low alcohol:water ratio, to produce a second series of step-wise eluates eluted at different alcohol:water ratios; and separating and identifying one of said second series of eluates as containing a substantially purified compound having anti-adherence activity.

14. A method of using a proanthocyanidin having a structure selected from I, II and III

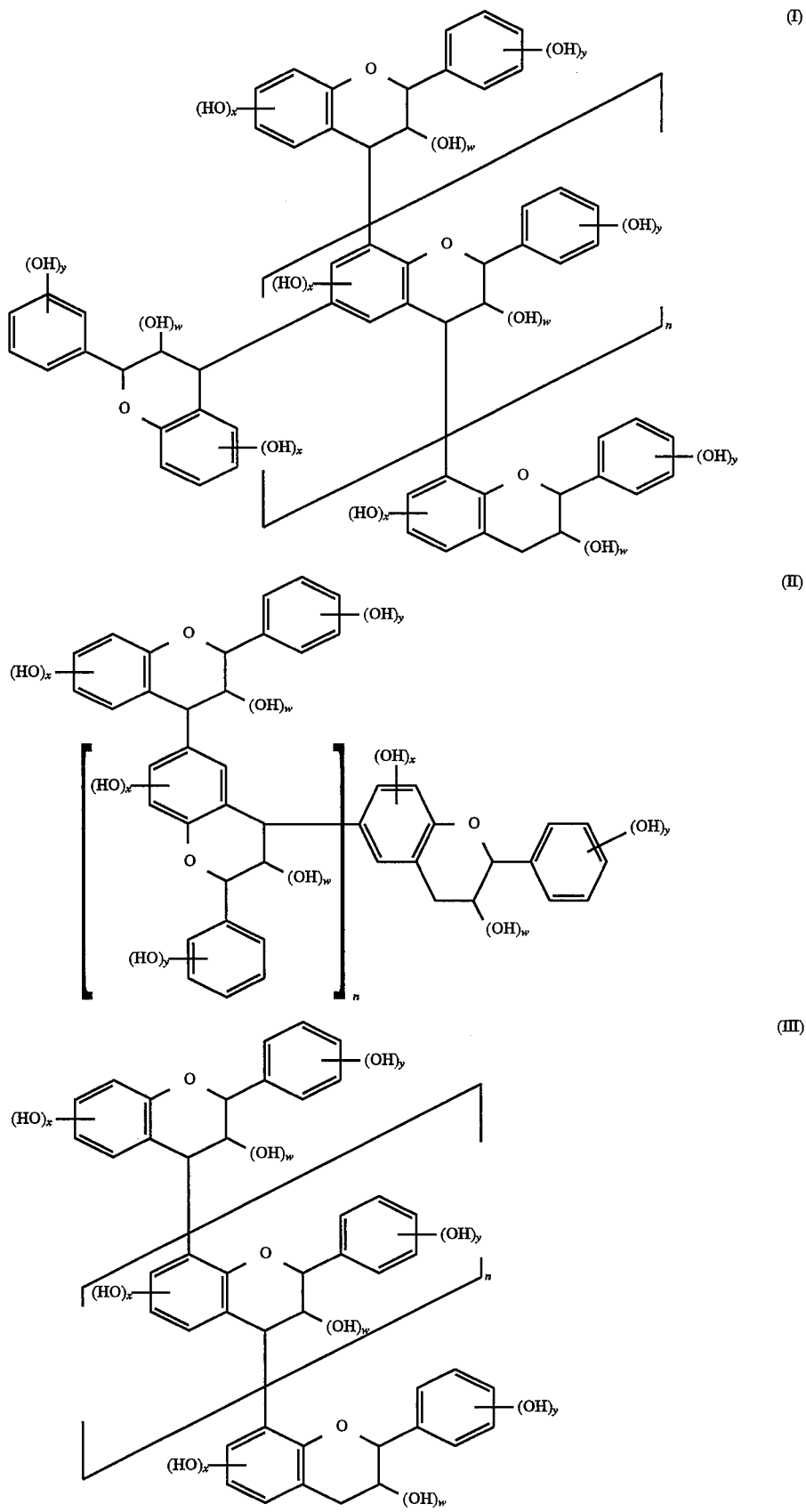
wherein x, y=1 to 3, w=0 or 1, n=0 to 18 comprising applying said proanthocyanidin to a surface of an inanimate object in an amount effective to interfere with microbial adhesion to the surface of said inanimate object.

15. The method of claim 14, wherein said inanimate object is selected from the group consisting of: biological fermentation equipment, medical instruments, dental instruments, surgical implants, and laboratory culture equipment.

16. An extract of plant material including a proanthocyanidin which is derived from said plant material, wherein said plant-derived proanthocyanidin is present in an proportion by dry weight of said extract which significantly exceeds a dry weight proportion of said proanthocyanidin in said plant material and has a structure selected from I, II, and III

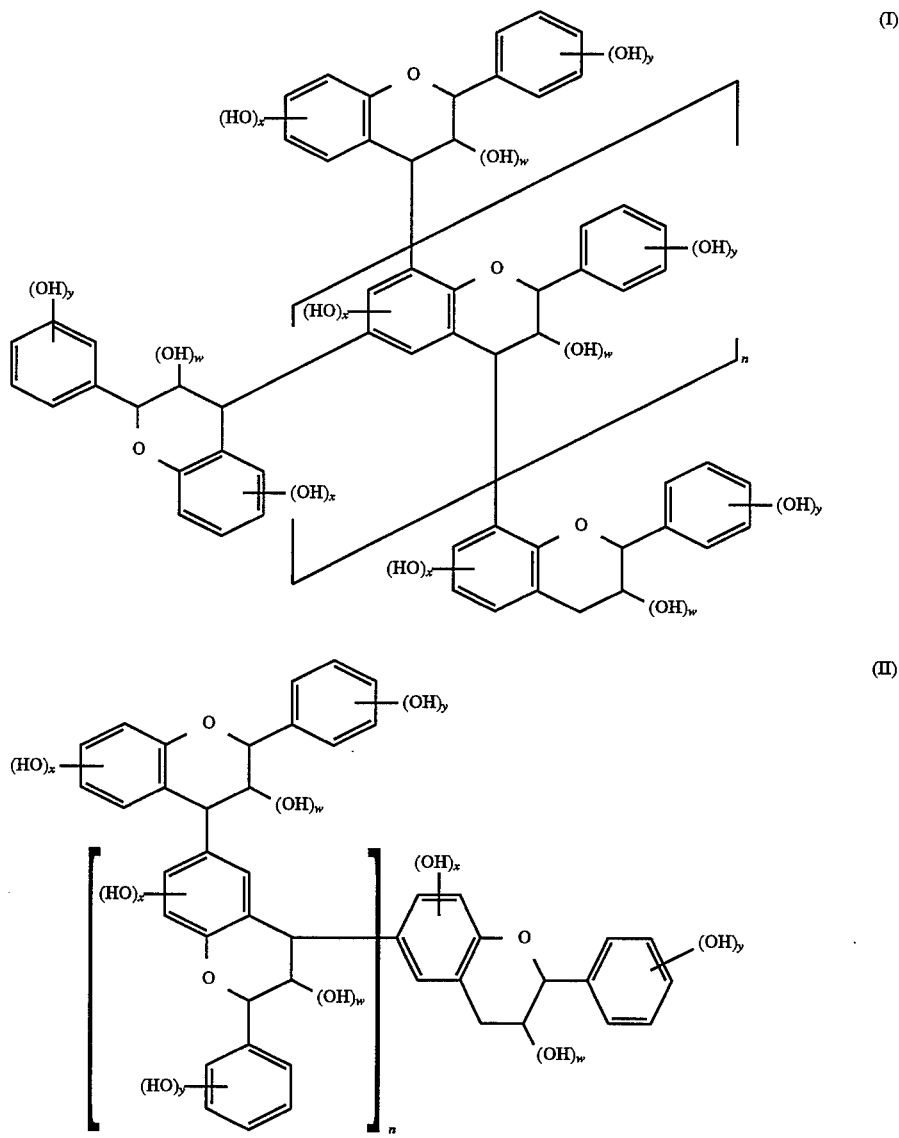

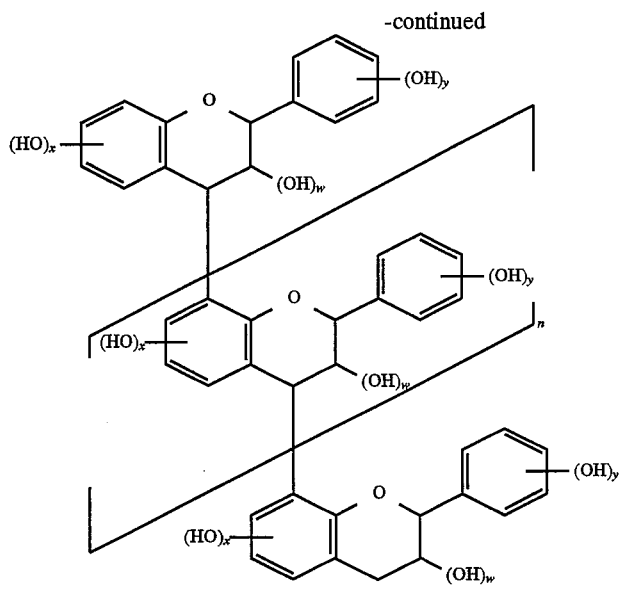

(III)

wherein x, y=1 to 3, w=0 or 1, n=0 to 18.

17. The extract of claim 16, wherein said plant material is from a plant of the genus Vaccinium.

18. The extract of claim 16, which further includes a compound comprising structure IV

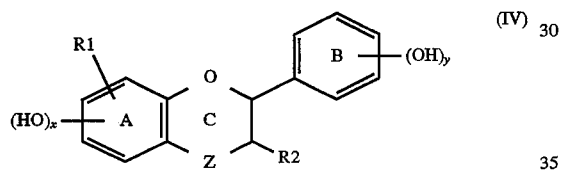

(IV)

wherein x is 0 to 3; y is 0 to 3; Z is $CH_2$, CHOH, C=O, $CHSO_3H$, galloyl, catechin, or epicatechin: $R_1$ is H, pyranoside, galloyl, catechin, or epicatechin; and R2=galloyl.

19. A plant extract having an active fraction which is active to inhibit adherence of microbes to cell surfaces, obtainable by a process comprising:

providing a homogenate of a plant material of a plant having a native active fraction comprising polyphenolic compounds having anti-adherence activity;

adding a sufficient amount of a base to said homogenate to alkalinize said homogenate to a pH of greater than about pH 10 and to cause phenol groups of polyphenolic compounds to be ionized to phenoxide ions; and adding to said alkalinized homogenate, a sufficient amount of an organic solvent to produce a precipitate of said polyphenolic compounds having phenoxide ions, and separating said precipitate.

20. The extract of claim 19, wherein said process further comprises:

fractionating said precipitate on a lipophilic column by step-wise elution with solutions containing varying ratios of an organic solvent to water, said organic solvent being water-miscible, beginning with a low organic solvent:water ratio, to produce a series of step-wise eluates eluted at different organic solvent-:water ratios; and separating and identifying one of said eluates as substantially comprising said fraction having anti-adherence activity.

21. The extract of claim 19, wherein said process further comprises:

fractionating said anti-adherence eluate on a column to separate substantially colorless polyphenolic compounds from colored anthocyanic compounds;

fractionating the colorless polyphenolic compounds recovered from said column on a second lipophilic column by step-wise elution with solutions containing varying ratios of an organic solvent to water, said organic solvent being water-miscible, beginning with a low organic solvent:water ratio, to produce a second series of step-wise eluates eluted at different organic solvent:water ratios; and separating and identifying one of said second series of eluates as having anti-adherence activity.

22. A composition comprising:

a proanthocyanidin having a structure selected from I, II and III

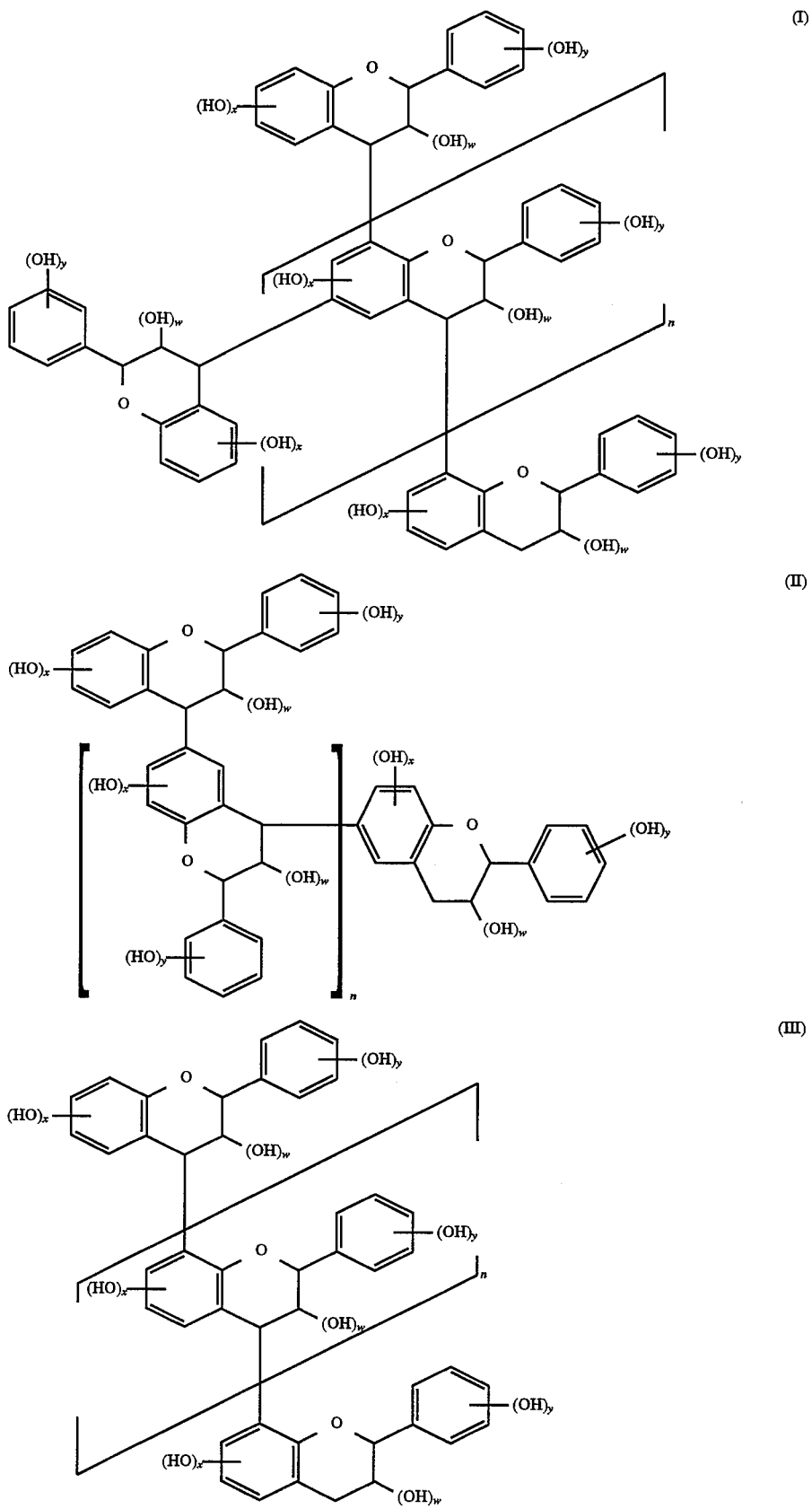

wherein x, y=1 to 3, w=0 or 1, n=0 to 18, in an amount effective to interfere with microbial adhesion to biological surfaces; and an appropriate carrier.

23. The composition of claim 22, which is an oral hygiene product and wherein said carrier is a topical carrier selected from the group consisting of dental paste, powder, gel base compositions, aqueous solutions, aqueous-alcohol solutions suitable for oral rinsing or gargling, dental floss, artificial saliva and chewing gum.

24. The composition of claim 22, wherein said carrier comprises a tablet and wherein said composition is present in an amount of between about 0.5 milligram and about 500 milligrams.

25. The composition of claim 22, wherein said appropriate carrier is compatible with genital and cervical mucosal tissues and is selected from the group consisting of douches, suppository formulations, creams and jellies.

26. A composition comprising:

the composition of claim 22 in an amount effective to interfere with microbial adhesion to biological surfaces;

one or more additional compounds selected from the group consisting of polyphenols in an amount effective to enhance said anti-adhesion activity of said proanthocyanidin; and a pharmaceutically acceptable carrier.

27. The composition of claim 26, wherein said polyphenols include galloyl-substituted tannins and galloyl-substituted condensed polyphenols.

28. A composition comprising:

the extract of claim 16 in an amount effective to interfere with microbial adhesion to biological surfaces; and a pharmaceutically acceptable carrier.

29. A composition comprising:

the extract of claim 16 in an amount effective to interfere with microbial adhesion to a surface of an inanimate object; and a pharmaceutically acceptable carrier.

30. The composition of claim 29, wherein said inanimate object is selected from the group consisting of: biological fermentation equipment, medical instruments, dental instruments, surgical implants, and laboratory culture equipment.

31. A composition comprising:

a proanthocyanidin having a structure selected from I, II and

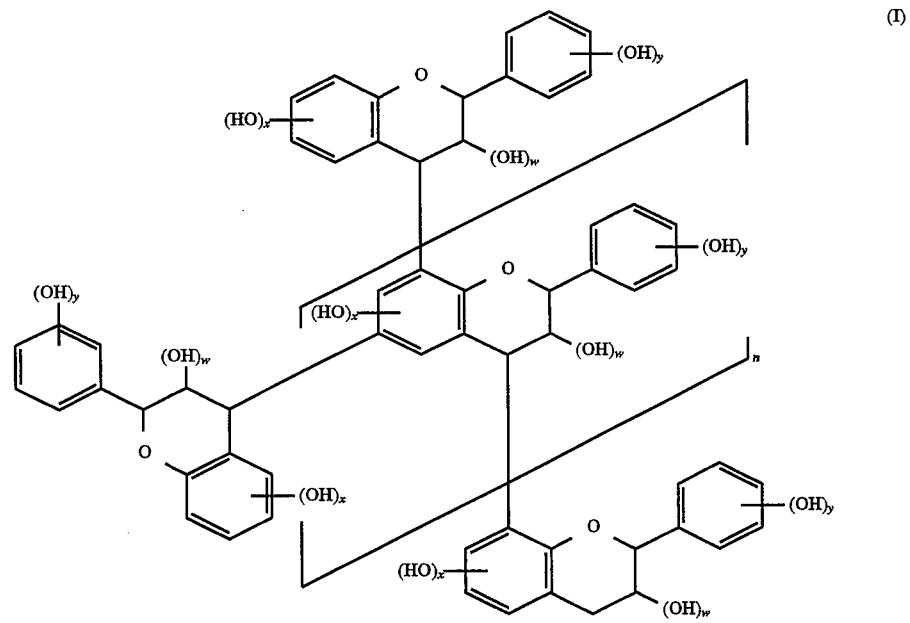

(I)

-continued

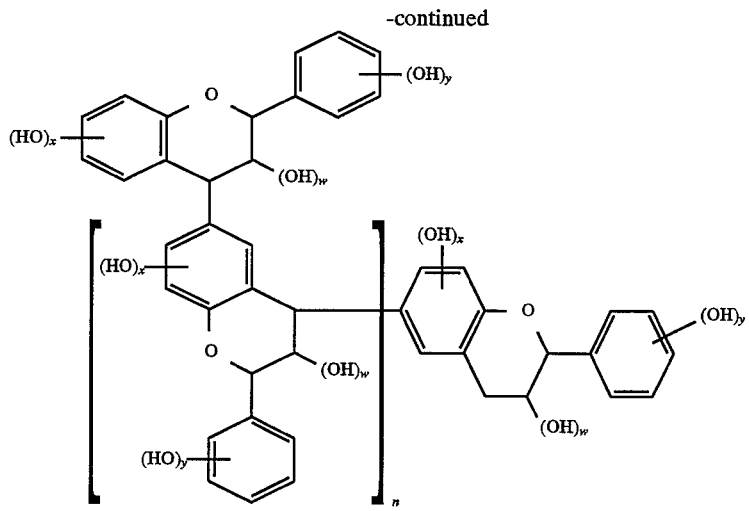

(II)

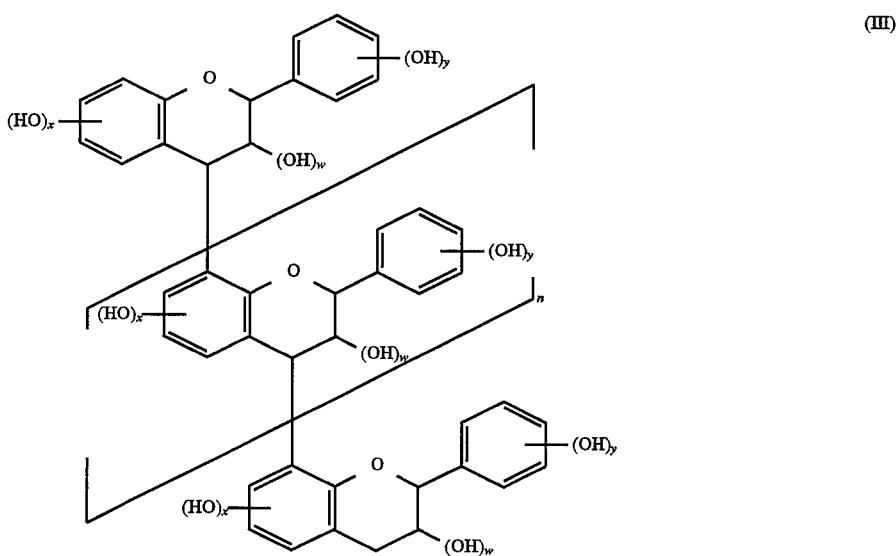

(III)

wherein x, y=1 to 3, w=0 or 1, n=0 to 18 in an amount effective to interfere with microbial adhesion to a surface of an inanimate object;

one or more additional compounds selected from the group consisting of polyphenols in an amount effective to enhance said anti-adhesion activity of said proanthocyanidin; and a carrier.

32. The composition of claim 31, wherein said inanimate object is selected from the group consisting of: biological fermentation equipment, medical instruments, dental instruments, surgical implants, and laboratory culture equipment.

33. The composition of claim 31, wherein said polyphenols include galloyl-substituted tannins and galloyl-substituted condensed polyphenols.

* * * * *

UNITED STATES PATENT AND TRADEMARK OFFICE
CERTIFICATE OF CORRECTION

PATENT NO. : 5,646,178
DATED : July 8, 1997
INVENTOR(S) : Walker et al.

It is certified that error appears in the above-identified patent and that said Letters Patent is hereby corrected as shown below:

Title Page, Col. 2, line 18, change "650" to --640--;

Col. 3, line 62, before "is CH" insert --Z--;

Col. 6, line 42, change "an" to --a--;

Col. 7, line 10, change "FIG" to --FIGS--;

Col. 10, line 31, change "bond" to --bound--;

Col. 10, line 34, change "pill" to --pili--;

Col. 13, line 15, change "anaqueous" to --aqueous--;

Col. 13, line 66, after "100" insert --ml--;

Col. 13, line 67, after "100" insert --ml--;

Col. 14, line 24, change "re, dissolved" to --redissolved--;

Col. 19, line 44, change "falter" to --filter--;

Col. 20, line 16, after "column" change "." (period) to --,-- (comma);

Col. 20, line 22, change "Light" to --light--;

Col. 22, line 21, change "$N_4OH$" to --$NH_4OH$--;

Col. 22, line 42, after "water" insert --(Step 112)--;

Col. 23, line 17, change "100mi" to --100ml--;

UNITED STATES PATENT AND TRADEMARK OFFICE
CERTIFICATE OF CORRECTION

PATENT NO. : 5,646,178
DATED : July 8, 1997
INVENTOR(S) : Walker et al.

It is certified that error appears in the above-identified patent and that said Letters Patent is hereby corrected as shown below:

Col. 24, line 2, after "in" delete "." (period);
Col. 24, line 20, change "1000" to --1001--;
Col. 24, line 37, change "I" to --is--;
Col. 24, line 55, change "1:IO" to --1:10--;
Col. 25, line 57, change "chromatogram" to --chromatograms--;
Col. 27, line 62, change "out" to --but--;
Col. 36, line 1, change "an" to --a--;
Col. 42, line 24, after "and" insert --III--.

Signed and Sealed this

Second Day of June, 1998

BRUCE LEHMAN

*Attest:*

*Attesting Officer*  Commissioner of Patents and Trademarks